United States Patent
Orozco, Jr. et al.

(10) Patent No.: US 6,323,015 B1
(45) Date of Patent: Nov. 27, 2001

(54) SUCROSE PHOSPHATE SYNTHASE

(75) Inventors: Emil M. Orozco, Jr., West Grove; Perry G. Caimi, Kennett Square, both of PA (US); Zude Weng, Des Plaines, IL (US); Mitchell C. Tarczynski, West Dest Moines, IA (US)

(73) Assignees: E. I. du Pont de Nemours & Company, Wilmington, DE (US); Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/697,367

(22) Filed: Oct. 26, 2000

Related U.S. Application Data

(63) Continuation of application No. PCT/US99/09865, filed on May 6, 1999.
(60) Provisional application No. 60/084,529, filed on May 7, 1998.

(51) Int. Cl.[7] ..................................................... C12N 9/10
(52) U.S. Cl. .................. 435/193; 435/252.3; 435/320.1; 435/410; 435/415; 536/23.2
(58) Field of Search ................................ 435/193, 252.3, 435/410, 415, 320.1; 536/23.2

(56) References Cited

U.S. PATENT DOCUMENTS 5,665,892   9/1997   Van Assche et al. ................ 800/205

FOREIGN PATENT DOCUMENTS 0 466 995 A2   1/1992   (EP) .

OTHER PUBLICATIONS

Jonathan Ingram et al., Plant Phys., vol. 115:113–121, 1997, Analysis of cDNA Clones Encoding Sucrose–Phosphate Synthase in Relation to Sugar Interconversions Associated with Dehydration in the Resurrection Plant Craterosstigma plantagineum Hochst.

EMBL Sequence Library Data Accession No: Y11821, Jun. 10, 1997, Ingram, J. et al., Analysis of cDNA Clones Encoding Sucrose–Phosphate Synthase in Relation to Sugar Interconversions Associated with Dehydration in the Resurrection Plant Craterosstigma plantagineum Hochst.

Joao Roberto Oliveira Do Nascimento et al., Planta, vol. 203:282–288, 1997, Banana scurose–phosphate synthase gene expression during fruit ripening.

Holger Hesse et al., Mol. Gen. Genet., vol. 247:515–520, 1995, Cloning and expression analysis of sucrose–phosphate synthase from sugar beet (Beta vulgaris L.).

Phillip S. Kerr et al., Planta, vol. 170:515–519, 1987, Resolution of two molecular forms of sucrose–phosphate synthase from maize, soybean and spinach leaves.

Ann C. Worrell et al., The Plant Cell, vol. 3:1121–1130, Oct. 1991, Expression of a Maize Sucrose Phosphate Synthase in Tomato Alters Leaf Carbohydrate Partitioning.

National Center for Biotechnology Information General Identifier No. 1854376, Feb. 13, 1999, Sakakibara, H.

National Center for Biotechnology Information General Identifier No. 1854378, Feb. 13, 1999, Sugiharto, B. et al., Differential Expression of Two Genes for Sucrose–Phosphate Synthase in Sugarcane: Molecular Cloning of the cDNAs and Comparative Analysis of Gene Expression.

National Center for Biotechnology Information General Identifier No. 168626, Apr. 27, 1993, Worrell, A. C. et al., Expression of a Miaze Sucrose Phosphate Synthase in Tomato Alters Leaf Carbohydrate Partitioning.

Nielsen et al. Unusual regulatory properties of sucrose–phosphate synthase purified from soybean (Glycine max) leaves. Physiologia Plantarum 76:309–314. (1989).*

Weber et al. Sucrose metabolism during cotyledon development of Vicia fala. Plant Journal, 9(6), 841–850. (1996).*

Weber et al. GenEmbl database—Accession #z56278 (1996).*

* cited by examiner

*Primary Examiner*—Ponnathapuachuta Murthy
*Assistant Examiner*—Yong Pak

(57) ABSTRACT

This invention relates to an isolated nucleic acid fragment encoding a sucrose phosphate synthase. The invention also relates to the construction of a chimeric gene encoding all or a portion of the sucrose phosphate synthase, in sense or antisense orientation, wherein expression of the chimeric gene results in production of altered levels of the sucrose phosphate synthase in a transformed host cell.

9 Claims, No Drawings

```
                            SEQUENCE LISTING

<160> NUMBER OF SEQ ID NOS:  24

<210> SEQ ID NO 1
<211> LENGTH: 2236
<212> TYPE: DNA
<213> ORGANISM: Catalpa speciosa

<400> SEQUENCE: 1
gcacgagaga tagaggagca gtggcgtttg tatgatggtt ttgatccaat actagagcgt      60
aaactacgtg ctaggattag gcgtaatgtc agctgttacg gaaggttcat gcctcgcatg     120
gttgtaattc cacctgggat ggaattccat cacatagttc cacatgatgg agacatggat     180
actgaagctg aagcaaacga agatggaaag tctccagaaa cacctatttg ggcagaggta     240
atgcgtttct tttcaaatcc aaggaagcct atgattcttg cacttgccag gccagatcca     300
aagaaaaacc tcactacctt ggtcaaagca tttggggaat gtcgaccact aagggagctt     360
gctaatctta ccttgataat gggtaataga gataatattg atgaaatgtc gggaaccaat     420
gcttcagttc ttctatcaat ccttaagatg attgacaagt atgatctcta tggtcaagtg     480
gcatatccta aacatcacaa gcaacatgat gttcctgaaa tttaccgtct agcagcaaag     540
accaaggtgt ttttcataaa tccagctttt atcgagcctt tgggcttac tctcattgag     600 gctacagcat atggtttgcc aattgttgcg acgaaaaatg gtggccctgt tgatatacac     660
aaggttctgg acaatggtct ccttgttgat ccccacaatc agcagtccat tgctgatgct     720
cttttgaagc tggttgcgga taagcatctc tgggcgaaat gtagagcaaa tggattaaaa     780
aatattcacc ttttttcatg gccagaacat tgtagaactt atctctccaa aatagcaagt     840
tgcaaaccaa ggcaacctcg ttggttgaga aatgacgatg atgatgaaaa ttcagaatca     900
gattcaccaa gtgactcctt gagggatata caagatatat ctttgaacct caagttctcc     960
tttgaaggag ataagaatga gaatcgggaa aatatcggtg gttccttaga ctctgaagac    1020
cgaaagagta agctagaaaa tgctgtattg acgtggtcta agggtgtggt gaaaggtgca    1080
caaaaatctg ggtctactga taaggagac cagaatccta atgctggtaa gttcccagca    1140
ttgaggagga gaaaacacat ttttgtgatt gctgtggata atgatgcaag tgctggtctt    1200
tctgaaagtg ttaaaaagat ctttgaggct gtggagaagg aaaaaagtga aggctcagtt    1260
ggatttatat tagctacgtc ctttaacatc acacaaacat gttcttttct ggtttcagaa    1320
ggattgaacc ccacagaatt tgacgcattt atatgcaata gtggcggtga tctttattac    1380
tcatctattc attcagaaaa taatccgttt gtggtggact tgtattatca ttcacatatt    1440
gaataccgat ggggaggga agggttgagg aagactttag tgcgttgggc agcttctata    1500
actgataaga ctggagaaaa ggaagaacac attattgttg aagatgaaga gcttcggcc    1560 gactactgct attcttttaa agttcaaaag cctggagtgg ttcccccagt aaaggaactt    1620
agaaagttga tgagaattca ggcactacga tgtcatgtca tccattgtca aatggaagt    1680 aagatcaacg taattccagt ttcggcttct cgttcccaag cactcaggta tctgtatctt    1740
cgctggggta tggacttgtc gaaagtagtt gttttgtcg gggaaagcgg agacagcgac    1800
```

-continued

```
tatgaaggtt tgcttggcgg cgttaacaag tctgtagtgc tgggcggagt ttgcaccaat    1860
gcgagcagcc aactccatgc caaccgaagc tatcctctca cagatgtcgt atattatgac    1920
agtcctaata ttaccagaac ctctgaagga tttagcagct cggatctccg agcctcgctg    1980
gcggaggtag gtgttctcaa gacctaaaat ttttgcttac cgccttgtac acatgttcag    2040
cttaaaataa taagcatcaa cttatggatt gcttcctgtt tataattcgg ctgcataatg    2100
atgtgttata ttttctcaat aaacctttga gatgagacca ttttttcttt gttgcccttt    2160
ctggaggaat tgaaactgta atgggacatg ttcaattttc tcctttgtca tacaagcaaa    2220
aaaaaaaaaa aaatca                                                    2236
```

<210> SEQ ID NO 2
<211> LENGTH: 668
<212> TYPE: PRT
<213> ORGANISM: Catalpa speciosa

<400> SEQUENCE: 2

```
Ala Arg Glu Ile Glu Glu Gln Trp Arg Leu Tyr Asp Gly Phe Asp Pro
  1               5                  10                  15

Ile Leu Glu Arg Lys Leu Arg Ala Arg Ile Arg Arg Asn Val Ser Cys
                 20                  25                  30

Tyr Gly Arg Phe Met Pro Arg Met Val Val Ile Pro Pro Gly Met Glu
             35                  40                  45

Phe His His Ile Val Pro His Asp Gly Asp Met Asp Thr Glu Ala Glu
         50                  55                  60

Ala Asn Glu Asp Gly Lys Ser Pro Glu Thr Pro Ile Trp Ala Glu Val
 65                  70                  75                  80

Met Arg Phe Phe Ser Asn Pro Arg Lys Pro Met Ile Leu Ala Leu Ala
                 85                  90                  95

Arg Pro Asp Pro Lys Lys Asn Leu Thr Thr Leu Val Lys Ala Phe Gly
            100                 105                 110

Glu Cys Arg Pro Leu Arg Glu Leu Ala Asn Leu Thr Leu Ile Met Gly
        115                 120                 125

Asn Arg Asp Asn Ile Asp Glu Met Ser Gly Thr Asn Ala Ser Val Leu
130                 135                 140

Leu Ser Ile Leu Lys Met Ile Asp Lys Tyr Asp Leu Tyr Gly Gln Val
145                 150                 155                 160

Ala Tyr Pro Lys His His Lys Gln His Asp Val Pro Glu Ile Tyr Arg
                165                 170                 175

Leu Ala Ala Lys Thr Lys Gly Val Phe Ile Asn Pro Ala Phe Ile Glu
            180                 185                 190

Pro Phe Gly Leu Thr Leu Ile Glu Ala Thr Ala Tyr Gly Leu Pro Ile
        195                 200                 205

Val Ala Thr Lys Asn Gly Gly Pro Val Asp Ile His Lys Val Leu Asp
    210                 215                 220

Asn Gly Leu Leu Val Asp Pro His Asn Gln Gln Ser Ile Ala Asp Ala
225                 230                 235                 240

Leu Leu Lys Leu Val Ala Asp Lys His Leu Trp Ala Lys Cys Arg Ala
                245                 250                 255

Asn Gly Leu Lys Asn Ile His Leu Phe Ser Trp Pro Glu His Cys Arg
            260                 265                 270

Thr Tyr Leu Ser Lys Ile Ala Ser Cys Lys Pro Arg Gln Pro Arg Trp
        275                 280                 285

Leu Arg Asn Asp Asp Asp Asp Glu Asn Ser Glu Ser Asp Ser Pro Ser
```

```
            290                 295                 300
Asp Ser Leu Arg Asp Ile Gln Asp Ile Ser Leu Asn Leu Lys Phe Ser
305                 310                 315                 320
Phe Glu Gly Asp Lys Asn Glu Asn Arg Glu Asn Ile Gly Gly Ser Leu
                325                 330                 335
Asp Ser Glu Asp Arg Lys Ser Lys Leu Glu Asn Ala Val Leu Thr Trp
                340                 345                 350
Ser Lys Gly Val Val Lys Gly Ala Gln Lys Ser Gly Ser Thr Asp Lys
                355                 360                 365
Gly Asp Gln Asn Pro Asn Ala Gly Lys Phe Pro Ala Leu Arg Arg Arg
                370                 375                 380
Lys His Ile Phe Val Ile Ala Val Asp Asn Asp Ala Ser Ala Gly Leu
385                 390                 395                 400
Ser Glu Ser Val Lys Lys Ile Phe Glu Ala Val Glu Lys Glu Lys Ser
                405                 410                 415
Glu Gly Ser Val Gly Phe Ile Leu Ala Thr Ser Phe Asn Ile Thr Gln
                420                 425                 430
Thr Cys Ser Phe Leu Val Ser Glu Gly Leu Asn Pro Thr Glu Phe Asp
                435                 440                 445
Ala Phe Ile Cys Asn Ser Gly Gly Asp Leu Tyr Tyr Ser Ser Ile His
                450                 455                 460
Ser Glu Asn Asn Pro Phe Val Val Asp Leu Tyr Tyr His Ser His Ile
465                 470                 475                 480
Glu Tyr Arg Trp Gly Glu Gly Leu Arg Lys Thr Leu Val Arg Trp
                485                 490                 495
Ala Ala Ser Ile Thr Asp Lys Thr Gly Glu Lys Glu His Ile Ile
                500                 505                 510
Val Glu Asp Glu Thr Ser Ala Asp Tyr Cys Tyr Ser Phe Lys Val
                515                 520                 525
Gln Lys Pro Gly Val Val Pro Pro Val Lys Glu Leu Arg Lys Leu Met
                530                 535                 540
Arg Ile Gln Ala Leu Arg Cys His Val Ile His Cys Gln Asn Gly Ser
545                 550                 555                 560
Lys Ile Asn Val Ile Pro Val Ser Ala Ser Arg Ser Gln Ala Leu Arg
                565                 570                 575
Tyr Leu Tyr Leu Arg Trp Gly Met Asp Leu Ser Lys Val Val Phe
                580                 585                 590
Val Gly Glu Ser Gly Asp Ser Asp Tyr Glu Gly Leu Leu Gly Gly Val
                595                 600                 605
Asn Lys Ser Val Val Leu Gly Gly Val Cys Thr Asn Ala Ser Ser Gln
                610                 615                 620
Leu His Ala Asn Arg Ser Tyr Pro Leu Thr Asp Val Val Tyr Tyr Asp
625                 630                 635                 640
Ser Pro Asn Ile Thr Arg Thr Ser Glu Gly Phe Ser Ser Ser Asp Leu
                645                 650                 655
Arg Ala Ser Leu Ala Glu Val Gly Val Leu Lys Thr
                660                 665
```

<210> SEQ ID NO 3
<211> LENGTH: 863
<212> TYPE: DNA
<213> ORGANISM: Hordeum vulgare

<400> SEQUENCE: 3

```
gcacgagctt cctcgatagt agaaagaagg ggaagaactg aaaaacaagt tatctttgaa      60
gacgcagaac actcctcaac atcttgcctt gcgtttagag tggtcaatcc aaattattta     120
cctcctttga aggagctgca gaagttgatg agaatccagt cactacgctg tcatgctctt     180
tataaccaca gtgctaccag gctatctgta attccaattc atgcatcacg ctcccaggct     240
ctaaggtacc tgtctgttcg ttggggcata gagttgcgaa acgtcgtgat tcttgtcggt     300
gaaagcggcg attcagatta cgaagagctg tttggaggcc ttcacaagac gatcgtcctg     360
aagggcgagt caacacacc cgcaaacaga atccacacgg tcaggcggta cccgctgcaa      420
gacgtcatcg cgctcgattg ctcgaacatc atcggggtcg agggctgcag caccgacgac     480
ctgaccccta ctctgaagac gctcggcata ccgacgaagt gacacataga catatatttt     540 tgccttttt tctttatacg atgagaggac cgaacaatat acgaatatag caaatatata      600
ctatcgtttc catgctggat ggaaataccg attttgcctg caagccgtgt tgtggccgtc     660
accttgagct gtgaataacg acattacgat catgttggcc ctgtcatgtg gaaattcggc     720
gatgaagaac gaatccagag caggagggaa atctgttgaa cgcttcaaaa gtgttgttaa     780
gagaacattt gaaggaagca ttgatccaaa aaaaaaaaaa aaaaaaata aactcgaggg      840 gggcccgtac acaaggtacg ccc                                              863

<210> SEQ ID NO 4
<211> LENGTH: 171
<212> TYPE: PRT
<213> ORGANISM: Hordeum vulgare

<400> SEQUENCE: 4

Ala Ser Ser Ile Val Glu Arg Arg Gly Arg Thr Glu Lys Gln Val Ile
  1               5                  10                  15

Phe Glu Asp Ala Glu His Ser Ser Thr Ser Cys Leu Ala Phe Arg Val
                 20                  25                  30

Val Asn Pro Asn Tyr Leu Pro Pro Leu Lys Glu Leu Gln Lys Leu Met
             35                  40                  45

Arg Ile Gln Ser Leu Arg Cys His Ala Leu Tyr Asn His Ser Ala Thr
 50                  55                  60

Arg Leu Ser Val Ile Pro Ile His Ala Ser Arg Ser Gln Ala Leu Arg
 65                  70                  75                  80

Tyr Leu Ser Val Arg Trp Gly Ile Glu Leu Arg Asn Val Val Ile Leu
                 85                  90                  95

Val Gly Glu Ser Gly Asp Ser Asp Tyr Glu Glu Leu Phe Gly Gly Leu
                100                 105                 110

His Lys Thr Ile Val Leu Lys Gly Glu Phe Asn Thr Pro Ala Asn Arg
            115                 120                 125

Ile His Thr Val Arg Arg Tyr Pro Leu Gln Asp Val Ile Ala Leu Asp
130                 135                 140

Cys Ser Asn Ile Ile Gly Val Glu Gly Cys Ser Thr Asp Asp Leu Thr
145                 150                 155                 160

Pro Thr Leu Lys Thr Leu Gly Ile Pro Thr Lys
                165                 170

<210> SEQ ID NO 5
<211> LENGTH: 511
<212> TYPE: DNA
<213> ORGANISM: Zea mays
<220> FEATURE:
<221> NAME/KEY: unsure
<222> LOCATION: (169)
```

<221> NAME/KEY: unsure
<222> LOCATION: (333)
<221> NAME/KEY: unsure
<222> LOCATION: (379)
<221> NAME/KEY: unsure
<222> LOCATION: (404)
<221> NAME/KEY: unsure
<222> LOCATION: (406)
<221> NAME/KEY: unsure
<222> LOCATION: (409)
<221> NAME/KEY: unsure
<222> LOCATION: (431)
<221> NAME/KEY: unsure
<222> LOCATION: (491)
<221> NAME/KEY: unsure
<222> LOCATION: (494)
<221> NAME/KEY: unsure
<222> LOCATION: (496)
<221> NAME/KEY: unsure
<222> LOCATION: (506)

<400> SEQUENCE: 5

| | | | | | |
|---|---|---|---|---|---|
| cagaaacctc | caggatccga | ctccaatcga | atcgccaaag | cagacagggg | cgctcgcggg | 60 |
| ggcgccgagc | tcgacggggc | gagatggccg | ggaacgactg | gatcaacagc | tacctggagg | 120 |
| ctattctgga | cgctggcggg | gccgcgggag | atctctcggc | agccgcagna | gcgggacgg | 180 |
| ccgcgacgga | acgccgtgg | agaagcggga | taagtcgtcg | ctgatgctcc | gagagcgcgg | 240 |
| ccggttcagc | cccgcgcgat | acttcgtcga | ggaggtcatc | tccggcttcg | acgagaccga | 300 |
| cctctacaag | acctgggtcc | gcactcggct | atnaggagtc | cccaggaacg | gaacacgcgg | 360 |
| ctggagacat | gtcgtggang | attggaactc | ccaggaagaa | gaanantana | gagagaagct | 420 |
| acatttctaa | naacgcatga | tttagaaact | cgtaatatct | ctattgtcta | aactattgat | 480 |
| gagaaaggaa | ncantntatc | atcatnatga | g | | | 511 |

<210> SEQ ID NO 6
<211> LENGTH: 18
<212> TYPE: PRT
<213> ORGANISM: Zea mays

<400> SEQUENCE: 6

Met Ala Gly Asn Asp Trp Ile Asn Ser Tyr Leu Glu Ala Ile Leu Asp
 1               5                  10                  15

Ala Gly

<210> SEQ ID NO 7
<211> LENGTH: 1611
<212> TYPE: DNA
<213> ORGANISM: Zea mays
<220> FEATURE:
<221> NAME/KEY: unsure
<222> LOCATION: (14)
<221> NAME/KEY: unsure
<222> LOCATION: (1424)
<221> NAME/KEY: unsure
<222> LOCATION: (1469)
<221> NAME/KEY: unsure
<222> LOCATION: (1505)
<221> NAME/KEY: unsure
<222> LOCATION: (1515)
<221> NAME/KEY: unsure
<222> LOCATION: (1560)

<400> SEQUENCE: 7

| | | | | | |
|---|---|---|---|---|---|
| gggagtatac | agantggatc | tactaacaag | gcagatttct | gcacctgatg | ttgattggag | 60 |
| ttatggggaa | cctactgaga | tgctcagtcc | aataagttca | gaaaactttg | ggcttgagct | 120 |

-continued

```
gggcgaaagc agtggtgcct atattgtccg gataccattc ggaccaagag acaaatatat      180
ccctaaagag catctatggc ctcacatcca ggaatttgtt gatggcgcac ttgtccatat      240
catgcagatg tccaaggtcc ttggagaaca aattggtagt gggcaaccag tatggcctgt      300
tgttatacat ggacactatg ctgatgctgg tgattctgct gctttactgt ctggggcact      360
caatgtaccc atggtattca ctggtcattc tcttggcaga gataagttgg accagatttt      420
gaagcagggg cgtcaaacca gggatgaaat aaatgcaacc tataagataa tgcgtcgaat      480
tgaggccgag gaactttgcc ttgatacatc tgaaatcata attacaagta ccaggcaaga      540
aatagaacag caatggggat tatatgatgg ttttgatcta actatggccc ggaaactcag      600
agcaaggaat aaggcgtggt gtgagctgct tggtcgtta catgccccgt atgattgcaa       660
tccctcctgg catggagttt agtcatatag caccacatga tgttgacctc gacagtgagg      720
aaggaaatgg agatggctca ggttcaccag atccacctat ttgggctgat ataatgcgct      780
tcttctcaaa cccccggaag ccaatgattc ttgctcttgc tcgtccggat ccgaagaaga      840
atatcactac tctagtcaaa gcatttggtg aacatcgtga actgagaaat ttagcaaatc      900
ttacactgat caatggggaa accgtgatgg tcattgatga aatgtcaagc acaaatgcag      960
ctgttttgac ttcagcactc aagttaattg ataaatatga tctatatgga caagtggcat     1020
accccaagca ccataagcaa tctgaagttc ctgatattta tcgtttarct gcgagaacaa     1080
aaggagtttt tatcaattgg gcattgggtt gaaccaattg gactcaactt gattgaggct     1140
gctgcatatg gtctacccat ggttgccaac ccgaaatggt ggggcctgtg acaatacat      1200 ccgggttctt ggataatggg aaattcctgg gttgaccccc acaatcaaaa tgaaatagct     1260
gaggcacttt ataagcttgt gtcagataag cacttgtggt cacaatgtcg ccagaatggt     1320
ctgaaaaaca tccataaatt ttcatggcct gaacattgcc agaactattt ggcacgtgta     1380
gtcactctca agcctagaca tccccgctgg caaaagaatg atgntgcagc tgaaatatct     1440
gaagcagatt cacccgagga ctctttgang gatattcatg acatatcact taacttaaag     1500 cttttncttgg acagnggaaa atcaggcagc aaagaaggga attcaaatgc ttttgagaan     1560
gcattttgag gatgcagcgc aaaagttgca aggtggtaat gacatcaaaa a             1611
```

```
<210> SEQ ID NO 8
<211> LENGTH: 365
<212> TYPE: PRT
<213> ORGANISM: Zea mays
<220> FEATURE:
<221> NAME/KEY: UNSURE
<222> LOCATION: (5)
<221> NAME/KEY: UNSURE
<222> LOCATION: (205)
<221> NAME/KEY: UNSURE
<222> LOCATION: (356)

<400> SEQUENCE: 8

Gly Val Tyr Arg Xaa Asp Leu Leu Thr Arg Gln Ile Ser Ala Pro Asp
  1               5                  10                  15

Val Asp Trp Ser Tyr Gly Glu Pro Thr Glu Met Leu Ser Pro Ile Ser
             20                  25                  30

Ser Glu Asn Phe Gly Leu Glu Leu Gly Glu Ser Ser Gly Ala Tyr Ile
         35                  40                  45

Val Arg Ile Pro Phe Gly Pro Arg Asp Lys Tyr Ile Pro Lys Glu His
     50                  55                  60

Leu Trp Pro His Ile Gln Glu Phe Val Asp Gly Ala Leu Val His Ile
 65                  70                  75                  80
```

```
Met Gln Met Ser Lys Val Leu Gly Glu Gln Ile Gly Ser Gly Gln Pro
                85                  90                  95
Val Trp Pro Val Val Ile His Gly His Tyr Ala Asp Ala Gly Asp Ser
            100                 105                 110
Ala Ala Leu Leu Ser Gly Ala Leu Asn Val Pro Met Val Phe Thr Gly
        115                 120                 125
His Ser Leu Gly Arg Asp Lys Leu Asp Gln Ile Leu Lys Gln Gly Arg
    130                 135                 140
Gln Thr Arg Asp Glu Ile Asn Ala Thr Tyr Lys Ile Met Arg Arg Ile
145                 150                 155                 160
Glu Ala Glu Glu Leu Cys Leu Asp Thr Ser Glu Ile Ile Ile Thr Ser
                165                 170                 175
Thr Arg Gln Glu Ile Glu Gln Gln Trp Gly Leu Tyr Asp Gly Phe Asp
            180                 185                 190
Leu Thr Met Ala Arg Lys Leu Arg Ala Arg Asn Lys Xaa Gly Val Ser
        195                 200                 205
Cys Phe Gly Arg Tyr Met Pro Arg Met Ile Ala Ile Pro Pro Gly Met
    210                 215                 220
Glu Phe Ser His Ile Ala Pro His Asp Val Asp Leu Asp Ser Glu Glu
225                 230                 235                 240
Gly Asn Gly Asp Gly Ser Gly Ser Pro Asp Pro Ile Trp Ala Asp
                245                 250                 255
Ile Met Arg Phe Phe Ser Asn Pro Arg Lys Pro Met Ile Leu Ala Leu
            260                 265                 270
Ala Arg Pro Asp Pro Lys Lys Asn Ile Thr Thr Leu Val Lys Ala Phe
        275                 280                 285
Gly Glu His Arg Glu Leu Arg Asn Leu Ala Asn Leu Thr Leu Ile Asn
    290                 295                 300
Gly Glu Thr Val Met Val Ile Asp Glu Met Ser Ser Thr Asn Ala Ala
305                 310                 315                 320
Val Leu Thr Ser Ala Leu Lys Leu Ile Asp Lys Tyr Asp Leu Tyr Gly
                325                 330                 335
Gln Val Ala Tyr Pro Lys His His Lys Gln Ser Glu Val Pro Asp Ile
            340                 345                 350
Tyr Arg Leu Xaa Ala Arg Thr Lys Gly Val Phe Ile Asn
        355                 360                 365

<210> SEQ ID NO 9
<211> LENGTH: 661
<212> TYPE: DNA
<213> ORGANISM: Oryza sativa

<400> SEQUENCE: 9
gcacgaggaa gtgaagagct tctcaagcaa gggagacaga caagggagca aataaacatg      60
acatacaaaa taatgtgtag aattgaggca gaggagttgg ctcttgatgc atctgaaata     120
gttatagcaa gcactaggca agagataaa gagcaatgga atttgtatga cggttttgag     180
gtcatacttg caaggaaact ccgtgcaaga gtcaagcgtg gtgctaactg ctatggtcgc     240
tatatgcctc gtatggttat cattccccca ggtgttgaat tggccatat gattcatgac     300 ttcgatatag gatggtgaag aagaaaatcc atgtccagcc tctgaggacc cacccatttg     360
gtctcagata atgcgcttct ttacaaatcc taggaagcct atgattctgg ctgttgctcg     420
tccatatcct gaaagaata ttacatcact tgtaaaggca tttggtgaat gtcgccctct     480
```

-continued

```
aagggagcta gcaaatctga cactgataat gggtaaccgt gaggccattt ctaagatgaa    540
caacatgagt gctgctgtct tgacctcagt gcttacattg attgatgaat atgacttgta    600
tggtcaagtg gcttatccca agcatcataa gcactctgaa gttccagctt ctcaagcaag    660
g                                                                    661
```

<210> SEQ ID NO 10
<211> LENGTH: 210
<212> TYPE: PRT
<213> ORGANISM: Oryza sativa
<220> FEATURE:
<221> NAME/KEY: UNSURE
<222> LOCATION: (100)

<400> SEQUENCE: 10

```
Glu Glu Leu Leu Lys Gln Gly Arg Gln Thr Arg Glu Gln Ile Asn Met
  1               5                  10                  15

Thr Tyr Lys Ile Met Cys Arg Ile Glu Ala Glu Leu Ala Leu Asp
             20                  25                  30

Ala Ser Glu Ile Val Ile Ala Ser Thr Arg Gln Glu Ile Glu Glu Gln
         35                  40                  45

Trp Asn Leu Tyr Asp Gly Phe Glu Val Ile Leu Ala Arg Lys Leu Arg
     50                  55                  60

Ala Arg Val Lys Arg Gly Ala Asn Cys Tyr Gly Arg Tyr Met Pro Arg
 65                  70                  75                  80

Met Val Ile Ile Pro Pro Gly Val Glu Phe Gly His Met Ile His Asp
                 85                  90                  95

Phe Asp Ile Xaa Asp Gly Glu Glu Glu Asn Pro Cys Pro Ala Ser Glu
             100                 105                 110

Asp Pro Pro Ile Trp Ser Gln Ile Met Arg Phe Phe Thr Asn Pro Arg
         115                 120                 125

Lys Pro Met Ile Leu Ala Val Ala Arg Pro Tyr Pro Glu Lys Asn Ile
     130                 135                 140

Thr Ser Leu Val Lys Ala Phe Gly Glu Cys Arg Pro Leu Arg Glu Leu
145                 150                 155                 160

Ala Asn Leu Thr Leu Ile Met Gly Asn Arg Glu Ala Ile Ser Lys Met
                165                 170                 175

Asn Asn Met Ser Ala Ala Val Leu Thr Ser Val Leu Thr Leu Ile Asp
            180                 185                 190

Glu Tyr Asp Leu Tyr Gly Gln Val Ala Tyr Pro Lys His His Lys His
        195                 200                 205

Ser Glu
    210
```

<210> SEQ ID NO 11
<211> LENGTH: 546
<212> TYPE: DNA
<213> ORGANISM: Oryza sativa
<220> FEATURE:
<221> NAME/KEY: unsure
<222> LOCATION: (451)
<221> NAME/KEY: unsure
<222> LOCATION: (484)
<221> NAME/KEY: unsure
<222> LOCATION: (523)
<221> NAME/KEY: unsure
<222> LOCATION: (539)

<400> SEQUENCE: 11

```
cttacacctt gttgatccac atgatcagaa tgccattgca gatgcactgt ataagcttct    60
```

```
ttctgacaaa caactttggt cgagatgtag agagaatggg ctaaaaaata ttcaccagtt    120
ctcatggcct gaacattgca agaattactt gtcaaggata ttgacacttg gtccgagatc    180
acctgctatt ggtggcaaac aggaacagaa ggcacccata tcaggaagga agcatatcat    240
tgttatatct gtagactctg ttaacaagga agatctagtc cggataatca gaaacactat    300
tgaagtcaca cgcacagaaa aaatgtctgg ttcaactggg ttttgtgctg tcaacttcac    360
ttacaatatc aggagatacg cctcgctggc taagtgtctg caaggcatgt ttgcctactg    420
gttttttgga tgccttcaac ctgcaataag nggggaagtt aatatcctaa taccctttg     480 gtantcccgg gaagatacgc caaagcaagt tcccaaggtt acnccctggc aataagatnt    540
aaaatt                                                               546
```

<210> SEQ ID NO 12
<211> LENGTH: 112
<212> TYPE: PRT
<213> ORGANISM: Oryza sativa

<400> SEQUENCE: 12

```
Leu Val Asp Pro His Asp Gln Asn Ala Ile Ala Asp Ala Leu Tyr Lys
 1               5                  10                  15

Leu Leu Ser Asp Lys Gln Leu Trp Ser Arg Cys Arg Glu Asn Gly Leu
             20                  25                  30

Lys Asn Ile His Gln Phe Ser Trp Pro Glu His Cys Lys Asn Tyr Leu
         35                  40                  45

Ser Arg Ile Leu Thr Leu Gly Pro Arg Ser Pro Ala Ile Gly Gly Lys
     50                  55                  60

Gln Glu Gln Lys Ala Pro Ile Ser Gly Arg Lys His Ile Ile Val Ile
 65                  70                  75                  80

Ser Val Asp Ser Val Asn Lys Glu Asp Leu Val Arg Ile Ile Arg Asn
                 85                  90                  95

Thr Ile Glu Val Thr Arg Thr Glu Lys Met Ser Gly Ser Thr Gly Phe
            100                 105                 110
```

<210> SEQ ID NO 13
<211> LENGTH: 601
<212> TYPE: DNA
<213> ORGANISM: Oryza sativa
<220> FEATURE:
<221> NAME/KEY: unsure
<222> LOCATION: (308)
<221> NAME/KEY: unsure
<222> LOCATION: (393)
<221> NAME/KEY: unsure
<222> LOCATION: (463)
<221> NAME/KEY: unsure
<222> LOCATION: (467)
<221> NAME/KEY: unsure
<222> LOCATION: (484)
<221> NAME/KEY: unsure
<222> LOCATION: (498)
<221> NAME/KEY: unsure
<222> LOCATION: (504)
<221> NAME/KEY: unsure
<222> LOCATION: (506)
<221> NAME/KEY: unsure
<222> LOCATION: (582)
<221> NAME/KEY: unsure
<222> LOCATION: (587)
<221> NAME/KEY: unsure
<222> LOCATION: (593)
<221> NAME/KEY: unsure
<222> LOCATION: (600)

```
<400> SEQUENCE: 13
cttacatgta agctcgtgcc gaattcggca cgagcttaca ctttgtattc gggagatacg      60
ccaagcagtt cccaggttac tcctgcaata gatcaaaatc accaagcaca tattgagtat     120
cgatggggag gagaaggcct aagaaagtat ctagtgaaat gggctacttc agtggtagaa     180
agaaagggaa gaatcgaaag acaaattatt tttgaagacc ctgaacactc ttcaacctat     240
tgtcttgcat ttagagtggt caatccaaat catctacccc ctttaaagga gttgaggaaa     300
ttgatganaa tccaatcact ccgttgcaat gccttgtata accacagtgc caccagactc     360
tctgtagttc ccattcacgc atcacgttcc agncactaag tacttgtgta tacctgggga     420
atagactgca aatgttgcat cctgttggta aagtggcatc ggntatnaga cgctagtggc     480
tcanagacgt catctaaagg cgantnactc ccgcaacaat catacgtcag gaatacgtac     540
agagctccct gacactaata cattgcatga ggtaatcaat anagagnact cgncaattgn     600
g                                                                    601

<210> SEQ ID NO 14
<211> LENGTH: 118
<212> TYPE: PRT
<213> ORGANISM: Oryza sativa
<220> FEATURE:
<221> NAME/KEY: UNSURE
<222> LOCATION: (91)

<400> SEQUENCE: 14

Tyr Thr Leu Tyr Ser Gly Asp Thr Pro Ser Ser Gln Val Thr Pro
  1               5                  10                  15

Ala Ile Asp Gln Asn His Gln Ala His Ile Glu Tyr Arg Trp Gly Gly
                 20                  25                  30

Glu Gly Leu Arg Lys Tyr Leu Val Lys Trp Ala Thr Ser Val Val Glu
             35                  40                  45

Arg Lys Gly Arg Ile Glu Arg Gln Ile Ile Phe Glu Asp Pro Glu His
         50                  55                  60

Ser Ser Thr Tyr Cys Leu Ala Phe Arg Val Val Asn Pro Asn His Leu
 65                  70                  75                  80

Pro Pro Leu Lys Glu Leu Arg Lys Leu Met Xaa Ile Gln Ser Leu Arg
                 85                  90                  95

Cys Asn Ala Leu Tyr Asn His Ser Ala Thr Arg Leu Ser Val Val Pro
            100                 105                 110

Ile His Ala Ser Arg Ser
        115

<210> SEQ ID NO 15
<211> LENGTH: 3524
<212> TYPE: DNA
<213> ORGANISM: Glycine max

<400> SEQUENCE: 15
gcacgaggaa agtatttccg atgacataaa cttgtttgaa ttctccttgg cagcagcaag      60
aagcagagta taaatggcag gaaacgattg gctgaacagc taccttgaag ctatacttga     120
cgtgggtcct ggcctggacg atgccaagtc ctctcttctt ctccgagaga gaggcaggtt     180
cagccctact cgctacttcg tccaagaggt tattggcttc gatgagaccg atctctatcg     240
ctcttgggtt cgggcttcct ccaccaggag tcctcaggag aggaacacca ggctcgagaa     300
catgtgctgg cggatttgga acctcgctcg ccaaaagaag cagctggaga gtgagactgc     360
```

-continued

```
gctgagagtc aacaagcgtc gtttggagcg cgagcgggt cgcagggaag ccaccgctga      420
tatgtcggag gacttgtcgg aaggagagaa gggcgatccc ttgagtgact tgtccgctca     480
cggcggcgtc ggcgacttca accgatccag gttgcccaga atcagttccg ctgatgccat     540
ggagacttgg gccaacagtc agaaagggaa gaagctctac attgtgctca tcagcattca    600
tggcctaata cgaggcgaga atatggagct ggacgtgat tctgacacgg gtggtcaggt     660
taagtacgtt gtggaacttg caagggcatt gggatcaatg ccaggagttt atcgggttga    720
tttgctaact agacaagtgt cggcgccaga tgtagattgg agttatgggg agccgacgga    780
aatgttgtct ccaagagaca cagatgattt tggagatgac actggagaaa gcagtggttc    840
ttatatcgtt cgtattccct ttggtccaag agataaatat attccaaaag aacttctctg    900
gccttacatt cctgaatttg ttgatggagc gcttaaccac attatacaga tgtccaagtc    960
tcttggggaa cagattggca gtgggcatgc tgtctggcct gttgccatcc acggacatta    1020
tgcagatgca ggtgactctg ctgctcttct gtctggcgca ttaaatgttc caatgctttt    1080
tactggccac tcacttggcc gagataagtt ggaacaactt ttaaagcaag gtagactatc    1140
aaaggatgaa ataaacacaa cttacaagat tatgcgtagg attgaagctg aggaattggc    1200
ccttgatggt tctgaaatag tcatcacaag cactagacag gaaatagaag aacaatggcg    1260
cttgtatgat ggttttgatc ctgtattgga gcgtaaacta cgagcaagga tcaggcgtaa    1320
tgtgagctgc tatgggagat tcatgcctcg catggcgaca attccacctg gtatggagtt    1380
ccatcatatt gttccacacg atggtgatat agaaggtgaa ccagaaggaa atttggatca    1440
tcctgccccc caagatccac ctatttggtc tgagataatg cgcttcttta ccaaccctcg    1500
caagcctatg atacttgctc tcgctagacc agacccaaaa aagaacatca aactttggt    1560 aaaagcattt ggagaatgcc gtcctcttca agagcttgcc aaccttacat taattatggg    1620
taaccgagat ggaattgatg agatgtcaag cacaaatgct tctgttcttc tctcggtact    1680
taagttgatt gacaagtatg atctgtatgg gcaagtggca tatcctaaac atcacaaaca    1740
atatgatgtt cctgacatat atcgcctagc agcaaagaca aagggtgttt tcattaatcc    1800
agctttcatt gagccatttg gtcttacctt aattgaggca gctgctcatg gtttgccaat    1860
tgttgatact aaaaatggag gtcctgttga tattcatagg gtacttgaca atggtctgct    1920
cgtagatccc catgatcagc agtctattgc tgatgctctt ttgaagcttg ttagcaacaa    1980
acaactttgg gcaaaatgta gacagaatgg gttaaagaat attcatttat ttcatggcc    2040 cgagcactgt aagacttacc tttctaaaat agccacttgc aagccaaggc atccacaatg    2100
gcagcgaagt gaggatggag gtgaaagttc agaatcagat tcaccaggtg attccttgag    2160
agatttacag gacttgtctc taaatctgaa gttttcatta gatggagaga agagtgaggg    2220
tagtggaaat gacaattctt tgaattctga tggaaatgct gctgatagag gggcaaaatt    2280
agagaatgct gttttgtcat ggtcaaaggg catctctaag gacacacgca ggggtggggc    2340
tacagaaaaa tccgatcaga atccaaatgc tggtaaattt cctccattaa ggagaagaaa    2400
acatctgttt gtcattgctg tggattgtga taccacttca agccttcttg aaactattaa    2460
agccatcttt gagtctgctg gaaggatag ggcagagagc attgtaggtt tcatattgtc    2520
aacatcatta acaatatcag agatacagtc atttctaatc tcaggtggct tgagtcccat    2580
tgattttgat gcttatattt gcaatagtgg cagtgatcta ctatatccat ccctcaatcc    2640
cggagatcgc ccatttgtgg ttgacttgta ttaccactca cacattgaat accgttgggg    2700
tggagaaggg ttgaggaaga ctttagtgcg atgggctgat tcaatcactg ataagaaggg    2760
```

-continued

```
tgataatgac gaacaaattg tgagtcctgc tgaacagctt tctactgact actgttatgc     2820
tttcaaagtg cgaaagccag gaatggctcc ccctgtgaag gagcttcgca agttattacg     2880
gatccaagct ctgcgttgcc atccgatata ttgtcaaaat gggacaagac tgaatgtcat     2940
tccagtgctg gcatctcgtt cccaagccct cagatacctta tatgttcgat ggggttttga     3000
actgtcaaag atggtggtgt tcgttggaga atgcggtgac acagattacg aaggacttct     3060
tggtggccta cacaaaagtg tcatactgaa gggagtggga agcagtgcaa tcagtcaact     3120
ccataataac agaagctacc ctctttcaga tgtcacgcca ttggacagcc ccaacatcgt     3180
cgaggcaact gagggagta gcggtgctga tatccaggct ttgatcgaaa agtgggata      3240 tctcaatgga tgaaaaaatt tgaaagtcat ttctagttat atgcctctta gtgtgtgtct     3300
gctatgaaac ctacttctga gcaagcagat atctgaattt tatccacaat gttcataaag     3360
cttttttcct cctctcttct ctgtaacttc tatatcattc tcttcctcac aaacttcccc     3420
atgaaacata tttcctcttg tttccccact tatctccttg ttggttctgt atctacatat     3480 tacatttta atgaaggcca cttctcaaaa aaaaaaaaaa aaaa                      3524
```

<210> SEQ ID NO 16
<211> LENGTH: 1059
<212> TYPE: PRT
<213> ORGANISM: Glycine max

<400> SEQUENCE: 16

```
Met Ala Gly Asn Asp Trp Leu Asn Ser Tyr Leu Glu Ala Ile Leu Asp
  1               5                  10                  15

Val Gly Pro Gly Leu Asp Asp Ala Lys Ser Ser Leu Leu Leu Arg Glu
             20                  25                  30

Arg Gly Arg Phe Ser Pro Thr Arg Tyr Phe Val Gln Glu Val Ile Gly
         35                  40                  45

Phe Asp Glu Thr Asp Leu Tyr Arg Ser Trp Val Arg Ala Ser Ser Thr
     50                  55                  60

Arg Ser Pro Gln Glu Arg Asn Thr Arg Leu Glu Asn Met Cys Trp Arg
 65                  70                  75                  80

Ile Trp Asn Leu Ala Arg Gln Lys Lys Gln Leu Glu Ser Glu Thr Ala
                 85                  90                  95

Leu Arg Val Asn Lys Arg Arg Leu Glu Arg Glu Arg Gly Arg Arg Glu
            100                 105                 110

Ala Thr Ala Asp Met Ser Glu Asp Leu Ser Glu Gly Glu Lys Gly Asp
        115                 120                 125

Pro Leu Ser Asp Leu Ser Ala His Gly Gly Val Gly Asp Phe Asn Arg
    130                 135                 140

Ser Arg Leu Pro Arg Ile Ser Ser Ala Asp Ala Met Glu Thr Trp Ala
145                 150                 155                 160

Asn Ser Gln Lys Gly Lys Lys Leu Tyr Ile Val Leu Ile Ser Ile His
                165                 170                 175

Gly Leu Ile Arg Gly Glu Asn Met Glu Leu Gly Arg Asp Ser Asp Thr
            180                 185                 190

Gly Gly Gln Val Lys Tyr Val Val Glu Leu Ala Arg Ala Leu Gly Ser
        195                 200                 205

Met Pro Gly Val Tyr Arg Val Asp Leu Leu Thr Arg Gln Val Ser Ala
    210                 215                 220

Pro Asp Val Asp Trp Ser Tyr Gly Glu Pro Thr Glu Met Leu Ser Pro
225                 230                 235                 240
```

```
Arg Asp Thr Asp Asp Phe Gly Asp Asp Thr Gly Glu Ser Ser Gly Ser
            245                 250                 255

Tyr Ile Val Arg Ile Pro Phe Gly Pro Arg Asp Lys Tyr Ile Pro Lys
            260                 265                 270

Glu Leu Leu Trp Pro Tyr Ile Pro Glu Phe Val Asp Gly Ala Leu Asn
            275                 280                 285

His Ile Ile Gln Met Ser Lys Ser Leu Gly Glu Gln Ile Gly Ser Gly
            290                 295                 300

His Ala Val Trp Pro Val Ala Ile His Gly His Tyr Ala Asp Ala Gly
305                 310                 315                 320

Asp Ser Ala Ala Leu Leu Ser Gly Ala Leu Asn Val Pro Met Leu Phe
            325                 330                 335

Thr Gly His Ser Leu Gly Arg Asp Lys Leu Glu Gln Leu Leu Lys Gln
            340                 345                 350

Gly Arg Leu Ser Lys Asp Glu Ile Asn Thr Thr Tyr Lys Ile Met Arg
            355                 360                 365

Arg Ile Glu Ala Glu Leu Ala Leu Asp Gly Ser Glu Ile Val Ile
370                 375                 380

Thr Ser Thr Arg Gln Glu Ile Glu Glu Gln Trp Arg Leu Tyr Asp Gly
385                 390                 395                 400

Phe Asp Pro Val Leu Glu Arg Lys Leu Arg Ala Arg Ile Arg Arg Asn
            405                 410                 415

Val Ser Cys Tyr Gly Arg Phe Met Pro Arg Met Ala Thr Ile Pro Pro
            420                 425                 430

Gly Met Glu Phe His His Ile Val Pro His Asp Gly Asp Ile Glu Gly
            435                 440                 445

Glu Pro Glu Gly Asn Leu Asp His Pro Ala Pro Gln Asp Pro Pro Ile
450                 455                 460

Trp Ser Glu Ile Met Arg Phe Phe Thr Asn Pro Arg Lys Pro Met Ile
465                 470                 475                 480

Leu Ala Leu Ala Arg Pro Asp Pro Lys Lys Asn Ile Thr Thr Leu Val
            485                 490                 495

Lys Ala Phe Gly Glu Cys Arg Pro Leu Gln Glu Leu Ala Asn Leu Thr
            500                 505                 510

Leu Ile Met Gly Asn Arg Asp Gly Ile Asp Glu Met Ser Ser Thr Asn
            515                 520                 525

Ala Ser Val Leu Leu Ser Val Leu Lys Leu Ile Asp Lys Tyr Asp Leu
            530                 535                 540

Tyr Gly Gln Val Ala Tyr Pro Lys His His Lys Gln Tyr Asp Val Pro
545                 550                 555                 560

Asp Ile Tyr Arg Leu Ala Ala Lys Thr Lys Gly Val Phe Ile Asn Pro
            565                 570                 575

Ala Phe Ile Glu Pro Phe Gly Leu Thr Leu Ile Glu Ala Ala Ala His
            580                 585                 590

Gly Leu Pro Ile Val Asp Thr Lys Asn Gly Gly Pro Val Asp Ile His
            595                 600                 605

Arg Val Leu Asp Asn Gly Leu Leu Val Asp Pro His Asp Gln Gln Ser
            610                 615                 620

Ile Ala Asp Ala Leu Leu Lys Leu Val Ser Asn Lys Gln Leu Trp Ala
625                 630                 635                 640

Lys Cys Arg Gln Asn Gly Leu Lys Asn Ile His Leu Phe Ser Trp Pro
            645                 650                 655
```

-continued

```
Glu His Cys Lys Thr Tyr Leu Ser Lys Ile Ala Thr Cys Lys Pro Arg
            660                 665                 670

His Pro Gln Trp Gln Arg Ser Glu Asp Gly Glu Ser Ser Glu Ser
        675                 680                 685

Asp Ser Pro Gly Asp Ser Leu Arg Asp Leu Gln Asp Leu Ser Leu Asn
    690                 695                 700

Leu Lys Phe Ser Leu Asp Gly Glu Lys Ser Glu Gly Ser Gly Asn Asp
705                 710                 715                 720

Asn Ser Leu Asn Ser Asp Gly Asn Ala Ala Asp Arg Gly Ala Lys Leu
                725                 730                 735

Glu Asn Ala Val Leu Ser Trp Ser Lys Gly Ile Ser Lys Asp Thr Arg
                740                 745                 750

Arg Gly Gly Ala Thr Glu Lys Ser Asp Gln Asn Pro Asn Ala Gly Lys
            755                 760                 765

Phe Pro Pro Leu Arg Arg Lys His Leu Phe Val Ile Ala Val Asp
    770                 775                 780

Cys Asp Thr Thr Ser Ser Leu Leu Glu Thr Ile Lys Ala Ile Phe Glu
785                 790                 795                 800

Ser Ala Gly Lys Asp Arg Ala Glu Ser Ile Val Gly Phe Ile Leu Ser
                805                 810                 815

Thr Ser Leu Thr Ile Ser Glu Ile Gln Ser Phe Leu Ile Ser Gly Gly
                820                 825                 830

Leu Ser Pro Ile Asp Phe Asp Ala Tyr Ile Cys Asn Ser Gly Ser Asp
            835                 840                 845

Leu Tyr Tyr Pro Ser Leu Asn Pro Gly Asp Arg Pro Phe Val Val Asp
850                 855                 860

Leu Tyr Tyr His Ser His Ile Glu Tyr Arg Trp Gly Gly Glu Gly Leu
865                 870                 875                 880

Arg Lys Thr Leu Val Arg Trp Ala Asp Ser Ile Thr Asp Lys Lys Gly
                885                 890                 895

Asp Asn Asp Glu Gln Ile Val Ser Pro Ala Glu Gln Leu Ser Thr Asp
            900                 905                 910

Tyr Cys Tyr Ala Phe Lys Val Arg Lys Pro Gly Met Ala Pro Pro Val
    915                 920                 925

Lys Glu Leu Arg Lys Leu Leu Arg Ile Gln Ala Leu Arg Cys His Pro
930                 935                 940

Ile Tyr Cys Gln Asn Gly Thr Arg Leu Asn Val Ile Pro Val Leu Ala
945                 950                 955                 960

Ser Arg Ser Gln Ala Leu Arg Tyr Leu Tyr Val Arg Trp Gly Phe Glu
                965                 970                 975

Leu Ser Lys Met Val Val Phe Val Gly Glu Cys Gly Asp Thr Asp Tyr
                980                 985                 990

Glu Gly Leu Leu Gly Leu His Lys Ser Val Ile Leu Lys Gly Val
            995                 1000                1005

Gly Ser Ser Ala Ile Ser Gln Leu His Asn Asn Arg Ser Tyr Pro Leu
    1010                1015                1020

Ser Asp Val Thr Pro Leu Asp Ser Pro Asn Ile Val Glu Ala Thr Glu
1025                1030                1035                1040

Gly Ser Ser Gly Ala Asp Ile Gln Ala Leu Ile Glu Lys Val Gly Tyr
                1045                1050                1055

Leu Asn Gly

<210> SEQ ID NO 17
```

```
<211> LENGTH: 646
<212> TYPE: DNA
<213> ORGANISM: Glycine max
<220> FEATURE:
<221> NAME/KEY: unsure
<222> LOCATION: (355)
<221> NAME/KEY: unsure
<222> LOCATION: (397)
<221> NAME/KEY: unsure
<222> LOCATION: (412)
<221> NAME/KEY: unsure
<222> LOCATION: (539)
<221> NAME/KEY: unsure
<222> LOCATION: (552)
<221> NAME/KEY: unsure
<222> LOCATION: (560)
<221> NAME/KEY: unsure
<222> LOCATION: (594)
<221> NAME/KEY: unsure
<222> LOCATION: (598)
<221> NAME/KEY: unsure
<222> LOCATION: (613)
<221> NAME/KEY: unsure
<222> LOCATION: (631)
<221> NAME/KEY: unsure
<222> LOCATION: (633)

<400> SEQUENCE: 17
aaacagtaga gttcctaaca tcaggcaatg ttcaagtgaa tgagtttgat gctttaattt        60
gcagtagtgg aagtcaagtt tactaccctg gcatcaatac agaagaagga aagcttttgc       120
ctgatccaga ttatgaggta catattgact atcgttgggg gtgtgaaggt cttaagaaaa       180
ccatttggaa acttatgaat ggtgatgaga acagccccat tgaggaagat ctcaaatcca       240
gcaatgcaca ttgcatctca tacaaaataa aggatcttag taaggcaaaa aaagttgatg       300
agttgaggca gaagcttagg atgagaggtc tacgttgtca tcctatgtac tgcangggggt       360
catctagaat gcatgtgatt cctcctcttg catctanagc ccaagcactc angtatccct       420
tgtacgttgg aggttgaacg ttgcaaacat gtactcaccc ttggagaaac ggggacacgg       480
attatgagga gatgattctg gaacccacaa gaccataatc atgaaggaat ggttctaang       540
gtcaaaagag tnctaagagn ccaggaacta caaagagatg tattgcccaa tganaccncc       600
tgtgcatcat tcnaacacca tgaaacatgc nancttgaca attcaa                      646
```

```
<210> SEQ ID NO 18
<211> LENGTH: 136
<212> TYPE: PRT
<213> ORGANISM: Glycine max
<220> FEATURE:
<221> NAME/KEY: UNSURE
<222> LOCATION: (116)
<221> NAME/KEY: UNSURE
<222> LOCATION: (130)
<221> NAME/KEY: UNSURE
<222> LOCATION: (135)

<400> SEQUENCE: 18

Glu Phe Leu Thr Ser Gly Asn Val Gln Val Asn Glu Phe Asp Ala Leu
 1               5                  10                  15

Ile Cys Ser Ser Gly Ser Gln Val Tyr Tyr Pro Gly Ile Asn Thr Glu
                20                  25                  30

Glu Gly Lys Leu Leu Pro Asp Pro Asp Tyr Glu Val His Ile Asp Tyr
            35                  40                  45

Arg Trp Gly Cys Glu Gly Leu Lys Lys Thr Ile Trp Lys Leu Met Asn
        50                  55                  60

Gly Asp Glu Asn Ser Pro Ile Glu Glu Asp Leu Lys Ser Ser Asn Ala
```

|   | 65 |   |   |   | 70 |   |   |   | 75 |   |   |   | 80 |
|---|---|---|---|---|---|---|---|---|---|---|---|---|---|
| His | Cys | Ile | Ser | Tyr | Lys | Ile | Lys | Asp | Leu | Ser | Lys | Ala | Lys | Val |
|   |   |   |   | 85 |   |   |   | 90 |   |   |   | 95 |

Asp Glu Leu Arg Gln Lys Leu Arg Met Arg Gly Leu Arg Cys His Pro
              100                 105                 110

Met Tyr Cys Xaa Gly Ser Ser Arg Met His Val Ile Pro Pro Leu Ala
          115                 120                 125

Ser Xaa Ala Gln Ala Leu Xaa Tyr
    130                 135

<210> SEQ ID NO 19
<211> LENGTH: 1445
<212> TYPE: DNA
<213> ORGANISM: Triticum aestivum

<400> SEQUENCE: 19

| gcatcacaaa | cactcagaag | ttcttgatat | ttatcgttta | gcagcgagaa | cgaagggtgc | 60 |
| ttttgtaaat | gtagcttact | ttgaacaatt | cggtgttacc | ttgatagagg | ctgccatgca | 120 |
| tggtttacct | gtaattgcaa | caaaaaatgg | agctcctgtt | gaaattcatc | aggtgctcaa | 180 |
| caatggtctc | cttgtcgatc | cacatgatca | gaatgccatt | gcagatgcac | tgtataaact | 240 |
| tctttccgag | aagcaacttt | ggtcaaggtg | cagagaaaat | ggactaaaaa | atattcacca | 300 |
| attttcctgg | cctgaacatt | gcaagaatca | cctgtcaagg | atattgactc | ttggcatgag | 360 |
| atctcctgct | gtcggtagcg | aagaggaaag | gagtaaggca | cctatatcag | gaaggaagca | 420 |
| tatcattgtt | atttctgtag | actctgttaa | caaggagaat | ctagtgcgga | tcatcagaaa | 480 |
| tgcgattgag | gccgcacata | cagaaaacac | accggcttca | actggtttcg | tgctgtcaac | 540 |
| ttcgctaaca | atatcagaga | tatgttcact | gctagtatct | gtaggcatgc | atcctgctgg | 600 |
| ttttgatgct | tcatctgca | acagtgggag | tagcatttac | tatccttcat | attctggtaa | 660 |
| tacgccaagc | aattccaagg | ttacccatgt | aatagatcga | aatcatcaat | cacatattga | 720 |
| gtatcgttgg | ggaggagaag | gtctaagaaa | gtatcttgtg | aaatgggcta | cttcagtggt | 780 |
| tgaaagaaag | ggaagaattg | aaaggcaaat | gattttgaa | gattcagaac | actcttctac | 840 |
| atattgtctt | gcatttaaag | tggtgattcc | gattacgaag | agctgctagg | gggtctccac | 900 |
| aggaccataa | tcctgaaggg | cgacttcaac | attgctgcaa | acagaatcca | cacagtccgg | 960 |
| agataccct | tgcaggatgt | cgttgcactg | gacagctcca | acatcatcga | agtccagggt | 1020 |
| tgcactacag | aggacatcaa | gtctgccctg | cgtcagattg | gtgtgccgac | acaataacat | 1080 |
| ctttgcgcgc | accacgaa | aaggaagaag | aaaaggagag | gaagaacgag | ccaaaccgag | 1140 |
| cgccactatt | tccatacctg | atgggaatgt | cgattttgtt | tgtagattgt | agagtgtggg | 1200 |
| tgtggtatat | tctcgagctg | tgaataactt | cccacttttg | tttgtactat | tcacaaattt | 1260 |
| tgaagtggac | aatatcgata | atgtagtgg | gaaaacaaat | gtgagcagaa | aagtcatttg | 1320 |
| ggaactgaga | tgccccgaaa | atacagacaa | ggcgggagcc | taaatggatt | aactctgtct | 1380 |
| actcgtttta | ctggcaaaaa | aaaaaaaaaa | aaaaaaaaaa | aaaaaaaaaa | aaaaaaaaaa | 1440 |
| aaaaa |   |   |   |   |   | 1445 |

<210> SEQ ID NO 20
<211> LENGTH: 358
<212> TYPE: PRT
<213> ORGANISM: Triticum aestivum
<220> FEATURE:
<221> NAME/KEY: UNSURE

<222> LOCATION: (286)

<400> SEQUENCE: 20

```
His His Lys His Ser Glu Val Leu Asp Ile Tyr Arg Leu Ala Ala Arg
 1               5                  10                  15

Thr Lys Gly Ala Phe Val Asn Val Ala Tyr Phe Glu Gln Phe Gly Val
            20                  25                  30

Thr Leu Ile Glu Ala Ala Met His Gly Leu Pro Val Ile Ala Thr Lys
        35                  40                  45

Asn Gly Ala Pro Val Glu Ile His Gln Val Leu Asn Asn Gly Leu Leu
    50                  55                  60

Val Asp Pro His Asp Gln Asn Ala Ile Ala Asp Ala Leu Tyr Lys Leu
65                  70                  75                  80

Leu Ser Glu Lys Gln Leu Trp Ser Arg Cys Arg Glu Asn Gly Leu Lys
                85                  90                  95

Asn Ile His Gln Phe Ser Trp Pro Glu His Cys Lys Asn His Leu Ser
            100                 105                 110

Arg Ile Leu Thr Leu Gly Met Arg Ser Pro Ala Val Gly Ser Glu Glu
        115                 120                 125

Glu Arg Ser Lys Ala Pro Ile Ser Gly Arg Lys His Ile Ile Val Ile
    130                 135                 140

Ser Val Asp Ser Val Asn Lys Glu Asn Leu Val Arg Ile Ile Arg Asn
145                 150                 155                 160

Ala Ile Glu Ala Ala His Thr Glu Asn Thr Pro Ala Ser Thr Gly Phe
                165                 170                 175

Val Leu Ser Thr Ser Leu Thr Ile Ser Glu Ile Cys Ser Leu Leu Val
            180                 185                 190

Ser Val Gly Met His Pro Ala Gly Phe Asp Ala Phe Ile Cys Asn Ser
        195                 200                 205

Gly Ser Ser Ile Tyr Tyr Pro Ser Tyr Ser Gly Asn Thr Pro Ser Asn
    210                 215                 220

Ser Lys Val Thr His Val Ile Asp Arg Asn His Gln Ser His Ile Glu
225                 230                 235                 240

Tyr Arg Trp Gly Gly Glu Gly Leu Arg Lys Tyr Leu Val Lys Trp Ala
                245                 250                 255

Thr Ser Val Val Glu Arg Lys Gly Arg Ile Glu Arg Gln Met Ile Phe
            260                 265                 270

Glu Asp Ser Glu His Ser Ser Thr Tyr Cys Leu Ala Phe Xaa Ser Gly
        275                 280                 285

Asp Ser Asp Tyr Glu Glu Leu Leu Gly Gly Leu His Arg Thr Ile Ile
    290                 295                 300

Leu Lys Gly Asp Phe Asn Ile Ala Ala Asn Arg Ile His Thr Val Arg
305                 310                 315                 320

Arg Tyr Pro Leu Gln Asp Val Val Ala Leu Asp Ser Ser Asn Ile Ile
                325                 330                 335

Glu Val Gln Gly Cys Thr Thr Glu Asp Ile Lys Ser Ala Leu Arg Gln
            340                 345                 350

Ile Gly Val Pro Thr Gln
        355
```

<210> SEQ ID NO 21
<211> LENGTH: 1660
<212> TYPE: DNA
<213> ORGANISM: Triticum aestivum
<220> FEATURE:

-continued

```
<221> NAME/KEY: unsure
<222> LOCATION: (1323)
<221> NAME/KEY: unsure
<222> LOCATION: (1339)
<221> NAME/KEY: unsure
<222> LOCATION: (1393)
<221> NAME/KEY: unsure
<222> LOCATION: (1418)
<221> NAME/KEY: unsure
<222> LOCATION: (1453)
<221> NAME/KEY: unsure
<222> LOCATION: (1523)
<221> NAME/KEY: unsure
<222> LOCATION: (1530)
<221> NAME/KEY: unsure
<222> LOCATION: (1541)
<221> NAME/KEY: unsure
<222> LOCATION: (1560)
<221> NAME/KEY: unsure
<222> LOCATION: (1576)
<221> NAME/KEY: unsure
<222> LOCATION: (1579)
<221> NAME/KEY: unsure
<222> LOCATION: (1592)
<221> NAME/KEY: unsure
<222> LOCATION: (1599)
<221> NAME/KEY: unsure
<222> LOCATION: (1603)
<221> NAME/KEY: unsure
<222> LOCATION: (1614)
<221> NAME/KEY: unsure
<222> LOCATION: (1621)
<221> NAME/KEY: unsure
<222> LOCATION: (1631)

<400> SEQUENCE: 21
gcacgagccg ctgcttatgg tctgcccgtg gtggcaacca agaacggcgg gccggtggac      60
atcctcaagg cgcttcacaa cggcctgctg gtggacccgc actccgccga ggcgatcacc     120
ggcgcgctgc tcagcctgct ggccgacaag gggcagtggc tggagagccg acgcaacggc     180
ctgcgcaaca tccaccgctt ctcgtggccg caccactgcc gcctctacct ctcccacgtc     240
gccgcctact cgcaccaccc gtcgccgcac cagcggctcc gcgtccctgg cgtcccgtct     300
gcctcggcga gcatgggcgg tgacgactcc ctctcggact cactccgtgg cctctcgctc     360
caaatctccg tggacgcctc caacgacctc aatgccgggg actcggccgc gctgatcatg     420
gacgccctac gccgccgccc ggcggccgac aggcgcgagg gctccggcag ggcgttgggc     480
ttcgcgccgg gaaggaggca gaggctcctt gtcgtcgccg tcgactgcta cggcgatgac     540
ggcaagcccg acgtcgagca actgaagaaa gccatcgacg cggcgatgtc cgccagtgac     600
ggcgcgggag ggcggcaggg gtacgtgctc tcgaccggca tgaccatccc cgagaccgcg     660
gagacgctca aggcctgcgg cgccgacccg gccggcttcg acgcgctcat ttgcagcagc     720
ggcgcggaga tatgctaccc gtggaaggag ctgacggccg acgaggagta ctccggccac     780
gtggcgttcc ggtggcccgg cgaccacgtg aaaaccgtcg tgccgaggct cgggaaggcc     840
gacgacgcgc aggcgtccga cctcgccgtc gacgtgtccg ctggctccgt gcactgccac     900
gcctacgccg ccaccgacgc gtccaaggtg aagaaggtgg attcgatcag gcaggcgctg     960
cggatgcgcg ggttccggtg caacctcgtc tacacgcgcg cgtgcacgcg cctcaacgtc    1020
atccctctct ccgcttcccg cccacgcgcg ttgaggtacc tgtcgataca gtggggcatc    1080
gatctcgcca aggtggcggt gctcgtcggc gagaccggag acaccgaccg cgagaagctc    1140
ctgccggggc tgcacaagac gataactcct gccggggatg ctctcccaac ggcagcgaag    1200
cacctcgacc ccgacgagga cgagtacccc acccaggacg tcgtgcccat gactcaccca    1260
```

-continued

```
aacatcatca caatcggccg aagcccagcc tggcttttct aatttgacgc ggccgagaaa    1320
cantccgtac ggccgtacnc actgtaatcc tgggcaggaa gatgactgcc agaaaagtat    1380
aataaatttt aangatgtgc aaccatgaca acatgggnta aatttttagt ctaacatctc    1440
ccttcctgag gcnttgtcat atatatcact tataatgaac caagaaagaa tgcatgtgaa    1500
aaaacgatac aaactaactc tcncttaaan ctttggttaa natttgagat tctcacgtgn    1560
tcgtgactcg gtaaangant cggaaatttc cnattgacnc agnacccccg ccanccccct    1620
ngccccggtg nctaaaaggg ggaatttggg cccgaatccg                         1660
```

<210> SEQ ID NO 22
<211> LENGTH: 433
<212> TYPE: PRT
<213> ORGANISM: Triticum aestivum

<400> SEQUENCE: 22

```
Ala Arg Ala Ala Ala Tyr Gly Leu Pro Val Val Ala Thr Lys Asn Gly
  1               5                  10                  15

Gly Pro Val Asp Ile Leu Lys Ala Leu His Asn Gly Leu Leu Val Asp
             20                  25                  30

Pro His Ser Ala Glu Ala Ile Thr Gly Ala Leu Leu Ser Leu Leu Ala
         35                  40                  45

Asp Lys Gly Gln Trp Leu Glu Ser Arg Arg Asn Gly Leu Arg Asn Ile
     50                  55                  60

His Arg Phe Ser Trp Pro His His Cys Arg Leu Tyr Leu Ser His Val
 65                  70                  75                  80

Ala Ala Tyr Cys Asp His Pro Ser Pro His Gln Arg Leu Arg Val Pro
                 85                  90                  95

Gly Val Pro Ser Ala Ser Ala Ser Met Gly Gly Asp Ser Leu Ser
            100                 105                 110

Asp Ser Leu Arg Gly Leu Ser Leu Gln Ile Ser Val Asp Ala Ser Asn
            115                 120                 125

Asp Leu Asn Ala Gly Asp Ser Ala Ala Leu Ile Met Asp Ala Leu Arg
        130                 135                 140

Arg Arg Pro Ala Ala Asp Arg Arg Glu Gly Ser Gly Arg Ala Leu Gly
145                 150                 155                 160

Phe Ala Pro Gly Arg Arg Gln Arg Leu Leu Val Val Ala Val Asp Cys
                165                 170                 175

Tyr Gly Asp Asp Gly Lys Pro Asp Val Glu Gln Leu Lys Lys Ala Ile
            180                 185                 190

Asp Ala Ala Met Ser Ala Ser Asp Gly Ala Gly Gly Arg Gln Gly Tyr
        195                 200                 205

Val Leu Ser Thr Gly Met Thr Ile Pro Glu Thr Ala Glu Thr Leu Lys
    210                 215                 220

Ala Cys Gly Ala Asp Pro Ala Gly Phe Asp Ala Leu Ile Cys Ser Ser
225                 230                 235                 240

Gly Ala Glu Ile Cys Tyr Pro Trp Lys Glu Leu Thr Ala Asp Glu Glu
                245                 250                 255

Tyr Ser Gly His Val Ala Phe Arg Trp Pro Gly Asp His Val Lys Thr
            260                 265                 270

Val Val Pro Arg Leu Gly Lys Ala Asp Asp Ala Gln Ala Ser Asp Leu
        275                 280                 285

Ala Val Asp Val Ser Ala Gly Ser Val His Cys His Ala Tyr Ala Ala
    290                 295                 300
```

-continued

```
Thr Asp Ala Ser Lys Val Lys Val Asp Ser Ile Arg Gln Ala Leu
305                 310                 315                 320

Arg Met Arg Gly Phe Arg Cys Asn Leu Val Tyr Thr Arg Ala Cys Thr
            325                 330                 335

Arg Leu Asn Val Ile Pro Leu Ser Ala Ser Arg Pro Arg Ala Leu Arg
                340                 345                 350

Tyr Leu Ser Ile Gln Trp Gly Ile Asp Leu Ala Lys Val Ala Val Leu
                355                 360                 365

Val Gly Glu Thr Gly Asp Thr Asp Arg Glu Lys Leu Leu Pro Gly Leu
370                 375                 380

His Lys Thr Ile Thr Pro Ala Gly Asp Ala Leu Pro Thr Ala Ala Lys
385                 390                 395                 400

His Leu Asp Pro Asp Glu Asp Glu Tyr Pro Thr Gln Asp Val Val Pro
                405                 410                 415

Met Thr His Pro Asn Ile Ile Thr Ile Gly Arg Ser Pro Ala Trp Leu
                420                 425                 430

Phe
```

<210> SEQ ID NO 23
<211> LENGTH: 1057
<212> TYPE: PRT
<213> ORGANISM: Citrus unshiu

<400> SEQUENCE: 23

```
Met Ala Gly Asn Asp Trp Ile Asn Ser Tyr Leu Glu Ala Ile Leu Asp
1               5                   10                  15

Val Gly Pro Gly Leu Asp Asp Ala Lys Ser Ser Leu Leu Leu Arg Glu
            20                  25                  30

Arg Gly Arg Phe Ser Pro Thr Arg Tyr Phe Val Glu Glu Val Ile Thr
        35                  40                  45

Gly Phe Asp Glu Thr Asp Leu His Arg Ser Trp Val Lys Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Gly Glu Ala
                85                  90                  95

Ala Gln Arg Met Ala Lys Arg Leu Glu Arg Glu Arg Gly Arg Arg
            100                 105                 110

Glu Ala Thr Ala Asp Met Ser Glu Asp Leu Ser Glu Gly Glu Lys Gly
        115                 120                 125

Asp Ile Val Ser Asp Val Ser Ala His Gly Asp Ser Thr Arg Ser Arg
    130                 135                 140

Leu Pro Arg Ile Ser Ser Val Asp Ala Met Glu Thr Trp Ile Ser Gln
145                 150                 155                 160

Gln Lys Gly Lys Lys Leu Tyr Ile Val Leu Ile Ser Ile His Gly Leu
                165                 170                 175

Ile Arg Gly Glu Asn Met Glu Leu Gly Arg Asp Ser Asp Thr Gly Gly
            180                 185                 190

Gln Val Lys Tyr Val Val Glu Leu Ala Arg Ala Leu Gly Ser Met Pro
        195                 200                 205

Gly Val Tyr Arg Val Asp Leu Leu Thr Arg Gln Val Ser Ala Pro Asp
    210                 215                 220

Val Asp Trp Ser Tyr Gly Glu Pro Thr Glu Met Leu Thr Pro Arg Asn
225                 230                 235                 240
```

```
Ser Asp Asp Phe Met Asp Asp Met Gly Glu Ser Ser Gly Ala Tyr Ile
            245                 250                 255

Ile Arg Ile Pro Phe Gly Pro Lys Asp Lys Tyr Ile Ala Lys Glu Leu
            260                 265                 270

Leu Trp Pro His Ile Pro Glu Phe Val Asp Gly Ala Leu Asn His Ile
            275                 280                 285

Ile Arg Met Ser Asn Val Leu Gly Glu Gln Ile Gly Gly Lys Pro
            290                 295                 300

Val Trp Pro Val Ala Ile His Gly His Tyr Ala Asp Ala Gly Asp Ser
305                 310                 315                 320

Ala Ala Leu Leu Ser Gly Ala Leu Asn Val Pro Met Leu Phe Thr Gly
                    325                 330                 335

His Ser Leu Gly Arg Asp Lys Leu Glu Gln Leu Leu Lys Gln Ala Arg
                    340                 345                 350

Leu Ser Arg Asp Glu Ile Asn Ala Thr Tyr Lys Ile Met Arg Arg Ile
                    355                 360                 365

Glu Ala Glu Glu Leu Ser Leu Asp Ala Ser Glu Ile Val Ile Thr Ser
370                 375                 380

Thr Arg Gln Glu Ile Glu Glu Gln Trp Arg Leu Tyr Asp Gly Phe Asp
385                 390                 395                 400

Pro Val Leu Glu Arg Lys Leu Arg Ala Arg Ile Lys Arg Asn Val Ser
                    405                 410                 415

Cys Tyr Gly Lys Phe Met Pro Arg Met Ala Ile Ile Pro Pro Gly Met
                    420                 425                 430

Glu Phe His His Ile Val Pro Gln Asp Gly Asp Met Asp Gly Glu Thr
                    435                 440                 445

Glu Gly Asn Glu Asp Asn Pro Ala Ser Pro Asp Pro Pro Ile Trp Ser
            450                 455                 460

Glu Ile Met Arg Phe Phe Thr Asn Pro Arg Lys Pro Val Ile Leu Ala
465                 470                 475                 480

Leu Ala Arg Pro Asp Pro Lys Lys Asn Ile Thr Thr Leu Val Lys Ala
                    485                 490                 495

Phe Gly Glu Cys Arg Pro Leu Arg Glu Leu Ala Asn Leu Thr Leu Ile
                    500                 505                 510

Met Gly Asn Arg Asp Gly Ile Asp Glu Met Ser Ser Thr Ser Ala Ser
            515                 520                 525

Val Leu Leu Ser Val Leu Lys Leu Ile Asp Lys Tyr Asp Leu Tyr Gly
            530                 535                 540

Gln Val Ala Tyr Pro Lys His His Lys Gln Ser Asp Val Pro Glu Ile
545                 550                 555                 560

Tyr Arg Leu Ala Ala Lys Thr Lys Gly Val Phe Ile Asn Pro Ala Phe
                    565                 570                 575

Ile Glu Pro Phe Gly Leu Thr Leu Ile Glu Ala Ala His Gly Leu
            580                 585                 590

Pro Ile Val Ala Thr Lys Asn Gly Gly Pro Val Asp Ile His Arg Val
            595                 600                 605

Leu Asp Asn Gly Leu Leu Val Asp Pro His Asp Gln Gln Ser Ile Ala
            610                 615                 620

Asp Ala Leu Leu Lys Leu Val Ala Gly Lys Gln Leu Trp Ala Arg Cys
625                 630                 635                 640

Arg Gln Asn Gly Leu Lys Asn Ile His Leu Phe Ser Trp Pro Glu His
                    645                 650                 655

Cys Lys Thr Tyr Leu Ser Arg Ile Ala Gly Cys Lys Pro Arg His Pro
```

-continued

```
                    660                 665                 670
Gln Trp Gln Arg Thr Asp Asp Gly Glu Thr Ser Glu Ser Asp Ser
                675                 680                 685

Pro Gly Asp Ser Leu Arg Asp Ile Gln Asp Ile Ser Leu Asn Leu Lys
            690                 695                 700

Phe Ser Leu Asp Gly Glu Lys Ser Gly Ala Ser Gly Asn Asp Asp Ser
705                 710                 715                 720

Leu Asp Ser Glu Gly Asn Val Ala Asp Arg Lys Ser Arg Leu Glu Asn
                725                 730                 735

Ala Val Leu Ala Trp Ser Lys Gly Val Leu Lys Asp Thr Arg Lys Ser
                740                 745                 750

Gly Ser Thr Asp Lys Val Asp Gln Asn Thr Gly Ala Ala Lys Phe Pro
                755                 760                 765

Ala Leu Arg Arg Arg Lys His Ile Phe Val Ile Ser Val Asp Cys Asp
            770                 775                 780

Ser Thr Thr Gly Leu Leu Asp Ala Thr Lys Lys Ile Cys Glu Ala Val
785                 790                 795                 800

Glu Lys Glu Arg Thr Glu Gly Ser Ile Gly Phe Ile Leu Ser Thr Ser
                805                 810                 815

Met Thr Ile Ser Glu Ile His Ser Phe Leu Val Ser Gly His Leu Ser
            820                 825                 830

Pro Ser Asp Phe Asp Ala Phe Ile Cys Asn Ser Gly Ser Asp Leu Tyr
            835                 840                 845

Tyr Ser Thr Leu Asn Ser Glu Asp Gly Pro Phe Val Val Asp Phe Tyr
        850                 855                 860

Tyr His Ser His Ile Glu Tyr Arg Trp Gly Gly Glu Gly Leu Arg Lys
865                 870                 875                 880

Thr Leu Val Arg Trp Ala Ser Gln Val Thr Asp Lys Lys Ala Glu Ser
                885                 890                 895

Gly Glu Lys Val Leu Thr Pro Ala Glu Gln Leu Ser Thr Asn Tyr Cys
                900                 905                 910

Tyr Ala Phe Ser Val Gln Lys Pro Gly Met Thr Pro Pro Val Lys Glu
            915                 920                 925

Leu Arg Lys Val Leu Arg Ile Gln Ala Leu Arg Cys His Val Ile Tyr
            930                 935                 940

Cys Gln Asn Gly Ser Arg Val Asn Val Ile Pro Val Leu Ala Ser Arg
945                 950                 955                 960

Ser Gln Ala Leu Arg Tyr Leu Tyr Leu Arg Trp Gly Val Glu Leu Ser
                965                 970                 975

Lys Met Val Val Phe Val Gly Glu Ser Gly Asp Thr Asp Tyr Glu Gly
            980                 985                 990

Leu Leu Gly Gly Val His Lys Thr Val Ile Leu Lys Gly Ile Cys Ser
        995                 1000                1005

Ser Ser Ser Asn Gln Ile His Ala Asn Arg Ser Tyr Pro Leu Ser Asp
    1010                1015                1020

Val Met Pro Ile Asp Ser Pro Asn Ile Val Gln Thr Pro Glu Asp Cys
1025                1030                1035                1040

Thr Thr Ser Asp Ile Arg Ser Ser Leu Glu Gln Leu Gly Leu Leu Lys
                1045                1050                1055

Val
```

<210> SEQ ID NO 24
<211> LENGTH: 368

```
<212> TYPE: PRT
<213> ORGANISM: Zea mays

<400> SEQUENCE: 24

Gly Val Tyr Arg Val Asp Leu Phe Thr Arg Gln Val Ser Ser Pro Asp
 1               5                  10                  15

Val Asp Trp Ser Tyr Gly Glu Pro Thr Glu Met Leu Cys Ala Gly Ser
            20                  25                  30

Asn Asp Gly Glu Gly Met Gly Glu Ser Gly Gly Ala Tyr Ile Val Arg
        35                  40                  45

Ile Pro Cys Gly Pro Arg Asp Lys Tyr Leu Lys Lys Glu Ala Leu Trp
    50                  55                  60

Pro Tyr Leu Gln Glu Phe Val Asp Gly Ala Leu Ala His Ile Leu Asn
65                  70                  75                  80

Met Ser Lys Ala Leu Gly Glu Gln Val Gly Asn Gly Arg Pro Val Leu
                85                  90                  95

Pro Tyr Val Ile His Gly His Tyr Ala Asp Ala Gly Asp Val Ala Ala
            100                 105                 110

Leu Leu Ser Gly Ala Leu Asn Val Pro Met Val Leu Thr Gly His Ser
        115                 120                 125

Leu Gly Arg Asn Lys Leu Glu Gln Leu Leu Lys Gln Gly Arg Met Ser
    130                 135                 140

Lys Glu Glu Ile Asp Ser Thr Tyr Lys Ile Met Arg Arg Ile Glu Gly
145                 150                 155                 160

Glu Glu Leu Ala Leu Asp Ala Ser Glu Leu Val Ile Thr Ser Thr Arg
                165                 170                 175

Gln Glu Ile Asp Glu Gln Trp Gly Leu Tyr Asp Gly Phe Asp Val Lys
            180                 185                 190

Leu Glu Lys Val Leu Arg Ala Arg Ala Arg Gly Val Ser Cys His
        195                 200                 205

Gly Arg Tyr Met Pro Arg Met Val Val Ile Pro Pro Gly Met Asp Phe
    210                 215                 220

Ser Asn Val Val Val His Glu Asp Ile Asp Gly Asp Gly Asp Val Lys
225                 230                 235                 240

Asp Asp Ile Val Gly Leu Glu Gly Ala Ser Pro Lys Ser Met Pro Pro
                245                 250                 255

Ile Trp Ala Glu Val Met Arg Phe Leu Thr Asn Pro His Lys Pro Met
            260                 265                 270

Ile Leu Ala Leu Ser Arg Pro Asp Pro Lys Lys Asn Ile Thr Thr Leu
        275                 280                 285

Val Lys Ala Phe Gly Glu Cys Arg Pro Leu Arg Glu Leu Ala Asn Leu
    290                 295                 300

Thr Leu Ile Met Gly Asn Arg Asp Asp Ile Asp Asp Met Ser Ala Gly
305                 310                 315                 320

Asn Ala Ser Val Leu Thr Thr Val Leu Lys Leu Ile Asp Lys Tyr Asp
                325                 330                 335

Leu Tyr Gly Ser Val Ala Phe Pro Lys His His Asn Gln Ala Asp Val
            340                 345                 350

Pro Glu Ile Tyr Arg Leu Ala Ala Lys Met Lys Gly Val Phe Ile Asn
        355                 360                 365
```

SUCROSE PHOSPHATE SYNTHASE

CROSS-REFERENCE TO RELATED APPLICATIONS

This application is a continuation application of International Application No. PCT/US99/09865 filed May 6, 1999, now pending, which claims priority benefit of U.S. Provisional Application No. 60/084,529 filed May 7, 1998. The entire contents of International Application No. PCT/US99/09865 filed May 6, 1999 and U.S. Provisional Application No. 60/084,529 filed May 7, 1998 are herein incorporated by reference.

FIELD OF THE INVENTION

This invention is in the field of plant molecular biology. More specifically, this invention pertains to nucleic acid fragments encoding a sucrose biosynthetic enzyme in plants and seeds.

BACKGROUND OF THE INVENTION

In plants photosynthetically fixed carbon is ultimately converted into two main carbohydrate products, sucrose and starch. Sucrose is the form in which most fixed carbon is exported from the photosynthetic cell. Sucrose is then translocated to various parts of the plant which have a need for this sugar such as regions of active growth and developing seeds or tubers. Sucrose is synthesized in the cytoplasm of photosynthetic cells from the precursor dihydroxyacetone phosphate (DiHOAcP). In the last two steps of sucrose biosynthesis UDP-glucose is converted to sucrose by the successive action of sucrose phosphate synthase (SPS) (E.C. 2.4.1.14) and sucrose phosphatase. By modulating the level of SPS in plants it may be possible to control carbon partitioning in photosynthetic cells. Accordingly, the availability of nucleic acid sequences encoding all or a portion of a sucrose phosphate synthase protein would facilitate studies to better understand carbon partitioning in plants.

Worrell, A. C. et al. ((1991) *Plant Cell* 3:1121–1130) describe a maize cDNA that encodes a sucrose phosphate synthase as confirmed by the ability of the cloned sequence to direct sucrose phosphate synthesis in *E. coli*.

SUMMARY OF THE INVENTION

The instant invention relates to isolated nucleic acid fragments encoding a sucrose biosynthetic enzyme. Specifically, this invention concerns an isolated nucleic acid fragment encoding a sucrose phosphate synthase. In addition, this invention relates to a nucleic acid fragment that is complementary to the nucleic acid fragment encoding a sucrose phosphate synthase.

An additional embodiment of the instant invention pertains to a polypeptide encoding all or a substantial portion of a sucrose phosphate synthase.

In another embodiment, the instant invention relates to a chimeric gene encoding a sucrose phosphate synthase, or to a chimeric gene that comprises a nucleic acid fragment that is complementary to a nucleic acid fragment encoding a sucrose phosphate synthase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a sucrose phosphate synthase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a sucrose phosphate synthase in a transformed host cell comprising: a) transforming a host cell with a chimeric gene comprising a nucleic acid fragment encoding a sucrose phosphate synthase; and b) growing the transformed host cell under conditions that are suitable for expression of the chimeric gene wherein expression of the chimeric gene results in production of altered levels of a sucrose phosphate synthase in the transformed host cell.

An additional embodiment of the instant invention concerns a method for obtaining a nucleic acid fragment encoding all or a substantial portion of an amino acid sequence encoding a sucrose phosphate synthase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 depicts the amino acid sequence alignment between the sucrose phosphate synthase from Catalpa clone ncs.pk0009.e3 (SEQ ID NO:2), soybean clone sfl1.pk0048.a12 (SEQ ID NO:16) and *Citrus unshiu* (NCBI General Identifier No. 3915023; SEQ ID NO:23). Amino acids which are conserved among all sequences are indicated with an asterisk (*). The Catalpa clone ncs.pk0009.e3 (SEQ ID NO:2) appears to be missing the coding region for approximately the first 390 amino acids of the protein so that for the alignment in that region, an asterisk would indicate identity of the amino acid at that particular position of the sucrose phosphate synthase enzyme from the soybean clone sfl1.pk0048.a12 (SEQ ID NO: 16) and *Citrus unshiu* (NCBI General Identifier No. 3915023, SEQ ID NO:23). Dashes are used by the program to maximize alignment of the sequences.

FIG. 2 depicts the amino acid sequence alignment between the corn sucrose phosphate synthase derived from the contig assembled from a portion of the cDNA insert in clones p0130.cwtaf69r, p0093.cssan39r, p0094.cssst68r, p0119.cmtoh35r and p0127.cntag51r (SEQ ID NO:8) and the corn sucrose phosphate synthase (NCBI General Identifier No. 168626; SEQ ID NO:24) disclosed in U.S. Pat. No. 5,665,892. Amino acids which are conserved between the two sequences are indicated with an asterisk (*). Dashes are used by the program to maximize alignment of the sequences.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone ncs.pk0009.e3 encoding a substantial portion of a Catalpa sucrose phosphate synthase.

SEQ ID NO:2 is the deduced amino acid sequence of a substantial portion of a Catalpa sucrose phosphate synthase derived from the nucleotide sequence of SEQ ID NO:1.

SEQ ID NO:3 is the nucleotide sequence comprising the entire cDNA insert in clone bsh1.pk0013.d3 encoding a substantial portion of a barley sucrose phosphate synthase.

SEQ ID NO:4 is the deduced amino acid sequence of a substantial portion of a barley sucrose phosphate synthase derived from the nucleotide sequence of SEQ ID NO:3.

SEQ ID NO:5 is the nucleotide sequence comprising a substantial portion of the cDNA insert in clone ceb5.pk0081.g10 encoding the N-terminal region of a corn sucrose phosphate synthase.

SEQ ID NO:6 is the deduced amino acid sequence of the N-terminal region of a corn sucrose phosphate synthase derived from the nucleotide sequence of SEQ ID NO:5.

SEQ ID NO:7 is the nucleotide sequence comprising a contig assembled from a portion of the cDNA insert in clones p0130.cwtaf69r, p0093.cssan39r, p0094.cssst68r, p0119.cmtoh35r and p0127.cntag51r encoding a substantial portion of a corn sucrose phosphate synthase.

SEQ ID NO:8 is the deduced amino acid sequence of a substantial portion of a corn sucrose phosphate synthase derived from the nucleotide sequence of SEQ ID NO:7.

SEQ ID NO:9 is the nucleotide sequence comprising a contig assembled from a portion of the cDNA insert in clones r1s12.pk0024.d8 and r10n.pk0002.e3 encoding a substantial portion of a rice sucrose phosphate synthase.

SEQ ID NO:10 is the deduced amino acid sequence of a substantial portion of a rice sucrose phosphate synthase derived from the nucleotide sequence of SEQ ID NO:9.

SEQ ID NO:11 is the nucleotide sequence comprising a portion of the cDNA insert in clone r10n.pk086.i23 encoding a substantial portion of a rice sucrose phosphate synthase.

SEQ ID NO:12 is the deduced amino acid sequence of a substantial portion of a rice sucrose phosphate synthase derived from the nucleotide sequence of SEQ ID NO:11.

SEQ ID NO:13 is the nucleotide sequence comprising a portion of the cDNA insert in clone r10n.pk0056.d5 encoding a substantial portion of a rice sucrose phosphate synthase.

SEQ ID NO:14 is the deduced amino acid sequence of a substantial portion of a rice sucrose phosphate synthase derived from the nucleotide sequence of SEQ ID NO:13.

SEQ ID NO:15 is the nucleotide sequence comprising the entire cDNA insert in clone sfl1.pk0048.a12 encoding an entire soybean sucrose phosphate synthase.

SEQ ID NO:16 is the deduced amino acid sequence of an entire soybean sucrose phosphate synthase derived from the nucleotide sequence of SEQ ID NO:15.

SEQ ID NO:17 is the nucleotide sequence comprising a portion of the cDNA insert in clone sfl1.pk0075.d7 encoding a substantial portion of a soybean sucrose phosphate synthase.

SEQ ID NO:18 is the deduced amino acid sequence of a substantial portion of a soybean sucrose phosphate synthase derived from the nucleotide sequence of SEQ ID NO:17.

SEQ ID NO:19 is the nucleotide sequence comprising a contig assembled from the entire cDNA insert in clone wr1.pk0028.h11 and a portion of the cDNA insert in clone wr1.pk0112.a8 encoding a substantial portion of a wheat sucrose phosphate synthase.

SEQ ID NO:20 is the deduced amino acid sequence of a substantial portion of a wheat sucrose phosphate synthase derived from the nucleotide sequence of SEQ ID NO:19.

SEQ ID NO:21 is the nucleotide sequence comprising a contig assembled from a portion of the cDNA insert in clones wkm1c.pk0002.g6 and wr1.pk0046.c10 encoding a substantial portion of a wheat sucrose phosphate synthase.

SEQ ID NO:22 is the deduced amino acid sequence of a substantial portion of a wheat sucrose phosphate synthase derived from the nucleotide sequence of SEQ ID NO:21.

SEQ ID NO:23 is the amino acid sequence of a *Citrus unshiu* sucrose phosphate synthase NCBI General Identifier No. 3915023.

SEQ ID NO:24 is the amino acid sequence of a corn sucrose phosphate synthase, positions 219 to 586, set forth in NCBI General Identifier No. 168626.

The Sequence Listing contains the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 85% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASERGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) with the default parameters (GAP PENALTY=01, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the sucrose phosphate synthase proteins as set forth in SEQ ID NOs:2, 4, 6, 8, 10, 12, 14, 16, 18, 20 and 22. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in-vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant MoL Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sucrose biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Sucrose Phosphate Synthase

| Enzyme | Clone | Plant |
|---|---|---|
| Sucrose Phosphate Synthase | ncs.pk0009.e3 | Catalpa |
| | bsh1.pk0013.d3 | Barley |
| | ceb5.pk0081.g10 | Corn |
| | Contig of | |
| | p0130.cwtaf69r | |
| | p0093.cssan39r | |
| | p0094.cssst68r | |
| | p0119.cmtoh35r | |
| | p0127.cntag51r | |
| | Contig of | Rice |
| | rls12.pk0024.d8 | |
| | r10n.pk0002.e3 | |
| | rl0n.pk086.i23 | |
| | rl0n.pk0056.d5 | |
| | sfl1.pk0048.a12 | Soybean |
| | sfl1.pk0075.d7 | |
| | Contig of | Wheat |
| | wrl.pk0112.a8 | |
| | wrl.pk0028.h11 | |
| | Contig of | |
| | wkm1c.pk0002.g6 | |
| | wrlpk0046.c10 | |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other sucrose phosphate synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed sucrose phosphate synthases are present at higher or lower levels than normal or in cell types or developmental stages in which they are not normally found. This would have the effect of altering the level of sucrose biosynthetic activity in those cells.

Overexpression of the sucrose phosphate synthase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of MRNA expression, Western analysis of protein expression, or phenotypic analysis.

For some applications it may be useful to direct the instant sucrose biosynthetic enzyme to different cellular compartments, or to facilitate its secretion from the cell. It is thus envisioned that the chimeric gene described above may be further supplemented by altering the coding sequence to encode a sucrose phosphate synthase with appropriate intracellular targeting sequences such as transit sequences (Keegstra, K. (1989) *Cell 56:247–253*), signal sequences or sequences encoding endoplasmic reticulum localization (Chrispeels, J. J., (1991) *Ann. Rev. Plant Phys. Plant Mol. Biol*. 42:21–53), or nuclear localization signals (Raikhel, N. (1992) *Plant Phys*. 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding a sucrose phosphate synthase in plants for some applications. In order to accomplish this, a chimeric gene designed for co-suppression of the instant sucrose biosynthetic enzyme can be constructed by linking a gene or gene fragment encoding a sucrose phosphate synthase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant sucrose phosphate synthase (or portions thereof) may be produced in heterologous host cells, particularly in the cells of microbial hosts, and can be used to prepare antibodies to the these proteins by methods well known to those skilled in the art. The antibodies are useful for detecting sucrose phosphate synthase in situ in cells or in vitro in cell extracts. Preferred heterologous host cells for production of the instant sucrose phosphate synthase are microbial hosts. Microbial expression systems and expression vectors containing regulatory sequences that direct high level expression of foreign proteins are well known to those skilled in the art. Any of these could be used to construct a chimeric gene for production of the instant sucrose phosphate synthase. This chimeric gene could then be introduced into appropriate microorganisms via transformation to provide high level expression of the encoded sucrose biosynthetic enzyme. An example of a vector for high level expression of the sucrose phosphate synthase in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J Hum. Genet*. 32:314–331).

The production and use of plant gene-derived probes for use in genetic mapping is described in R. Bematzky, R. and Tanksley, S. D. (1986) *Plant Mol. Biol. Reporter* 4(1) :37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet*. 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J Lab. Clin. Med*. 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res*. 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res*. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the sucrose phosphate synthase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a sucrose phosphate synthase can be identified and obtained. This mutant plant can then be used to determine or confirm the natural function of the sucrose phosphate synthase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1
Composition of cDNA Libraries; Isolation and Sequencing of cDNA Clones cDNA libraries representing mRNAs from various barley, corn, catalpa, rice, soybean and wheat tissues were prepared. The characteristics of the libraries are described below.

TABLE 2 cDNA Libraries from Barley, Corn, Catalpa, Rice, Soybean and Wheat

| Library | Tissue | Clone |
| --- | --- | --- |
| bsh1 | Barley Sheath, Developing Seedling | bsh1.pk0013.d3 |
| ceb5 | Corn Endosperm 30 Days After Pollination | ceb5.pk0081.g10 |
| ncs | *Catalpa speciosa* Developing Seed | ncs.pk0009.e3 |
| p0093 | Corn Stalk And Shank | p0093.cssan39r |
| p0094 | Corn Leaf Collar For The Ear Leaf And The Next Next Leaf Above And Below | p0094.cssst68r |
| p0119 | Corn Night Harvested Ear Shoot/W Husk: V-12 Stage | p0119.cmtoh35r |
| p0127 | Corn Nucellus Tissue, 5 Days After Silking | p0127.cntag51r |
| p0130 | Corn Wild-Type Internode Tissue | p0130.cwtaf69r |
| rl0n | Rice 15 Day Old Leaf* | rl0n.pk0002.e3 |
| | | rl0n.pk0056.d5 |
| | | rl0n.pk086.123 |
| rls12 | Rice Leaf 15 Days After Germination, 12 Hours After Infection Of *Magnaporthe grisea* Strain 4360-R-67 (avr2-yamo) | rls12.pk0024.d8 |
| sfl1 | Soybean Immature Flower | sfl1.pk0048.a12 |
| | | sfl1.pk0075.d7 |
| wkm1c | Wheat Kernel Malted 55 Hours at 22° C. | wkm1c.pk0002.g6 |
| wr1 | Wheat Root, 7 Day Old Seedling, Light Grown | wr1.pk0028.h11 |
| | | wr1.pk0046.c10 |
| | | wr1.pk0112.a8 |

*This library was normalized essentially as described in U.S. Pat. No. 5,482,845 cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2
Identification of cDNA Clones

ESTs encoding a sucrose biosynthetic enzyme were identified by conducting BLAST (Basic Local Alignment Search Tool; Altschul, S. F., et al., (1993) *J Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3
Characterization of cDNA Clones Encoding a Sucrose Phosphate Synthase The BLASTX search using the EST sequences from several clones revealed similarity of the proteins encoded by the cDNAs to sucrose phosphate synthase from different organisms. The BLAST results for each of these ESTs are shown in Table 3:

TABLE 3

BLAST Results for Clones Encoding Polypeptides Homologous to Sucrose Phosphate Synthase

| | | | GenBank | |
| --- | --- | --- | --- | --- |
| Clone | Protein | Organism | Accession No. | Blast pLog score |
| bsh1.pk0013.d3 | SPS | *Saccharum officinarum* | AB001338 | 68.00 |
| ceb5.pk0081.g10 | SPS | *Beta vulgaris* | X81975 | 20.40 |
| ncs.pk0009.e3 | SPS | *Solanum tuberosum* | X73477 | 46.52 |
| rls12.pk0024.d8 | SPS | *Saccharum officinarum* | AB001338 | 64.7 |
| sfl1.pk0048.a12 | SPS | *Actinidia deliciosa* | U85449 | 54.52 |
| sfl1.pk0075.d7 | SPS | *Craterostigma plantagineum* | Y11795 | 52.05 |
| sfl1.pk0080.c11 | SPS | *Vicia faba* | Z56278 | 30.70 |
| wkm1c.pk0002.g6 | SPS | *Oryza sativa* | U33175 | 30.00 |
| wr1.pk0028.h11 | SPS | *Saccharum officinarum* | AB001338 | 60.70 |

The sequence of the entire cDNA insert in clone ncs.pk0009.e3 was determined and is shown in SEQ ID NO:1; the deduced amino acid sequence of this cDNA is shown in SEQ ID NO:2. The sequence of the entire cDNA insert in clone bsh1.pk0013.d3 was determined and is shown in SEQ ID NO:3; the deduced amino acid sequence of this cDNA is shown in SEQ ID NO:4. Additional sequence of the cDNA insert in clone ceb5.pk0081.g10 was determined and is shown in SEQ ID NO:5; the deduced amino acid sequence of this portion of the cDNA insert is shown in SEQ ID:6. TBLASTN analysis of the proprietary plant EST database indicated that additional corn clones besides ceb5.pk0081.g10 encoded sucrose phosphate synthase. A contig was assembled using the sequence from a portion of the cDNA insert in clones p0130.cwtaf69r, p0093.cssan39r, p0094.cssst68r, p0119.cmtoh35r and p0127.cntag51r. The sequence of this contig is shown in SEQID NO:7; the deduced amino acid sequence of this contig is shown in SEQ ID NO:8. TBLASTN analysis of the proprietary plant EST database indicated that additional rice clones besides rls12.pk0024.d8 encoded sucrose phosphate synthase. These are clones r10n.pk0002.e3, r10n.pk086.i23 and r10n.pk0056.d5. A contig was assembled using the sequence from a portion of the cDNA insert in clones rls12.pk0024.d8 and r10n.pk0002.e3. The sequence of this contig is shown in SEQ ID NO:9; the deduced amino acid sequence of this contig is shown in SEQ ID NO10. The sequence of a portion of the cDNA insert in clone r10n.pk086.i23 is shown in SEQ ID NO:11; the deduced amino acid sequence of this portion of the cDNA insert is shown in SEQ ID NO:12. The sequence of a portion of the cDNA insert in clone r10n.pk0056.d5 is shown in SEQ ID NO:13; the deduced amino acid sequence of this portion of the cDNA insert is shown in SEQ ID NO:14. TBLASTN analysis of the proprietary plant EST database indicated that additional soybean clones besides sfl1.pk0048.a12 and sfl1.pk0075.d7 encoded sucrose phosphate synthase. These are clones sfl1.pk0080.c11, sdp3c.pk018.k22, sdp2c.pk021.o13 and sgc6c.pk001.14. The sequence of the entire cDNA insert in clone sfl1.pk0048.a12 was determined and is shown in SEQ ID NO:15; the deduced amino acid sequence of this cDNA is shown in SEQ ID NO: 16. The nucleotide sequence in SEQ ID NO:15 includes the sequences from clones sfl1.pk0080.c11 (which was previously listed separately), sdp3c.pk018.k22, sdp2c.pk021.o13 and sgc6c.pk001.14. The sequence of a portion of the cDNA insert in clone sfl1.pk0075.d7 is shown in SEQ ID NO:17; the deduced amino acid sequence of this portion of the cDNA insert is shown in SEQ ID NO:18. TBLASTN analysis of the proprietary plant EST database indicated that additional wheat clones besides wkm1c.pk0002.g6 and wr1.pk0028.h11 encoded sucrose phosphate synthase. These are clones wr1.pk0112.a8 and wr1.pk0046.c10. A contig was assembled using the sequence from the entire cDNA insert in clone wr1.pk0028.h11 and a portion of the cDNA insert in clone wr1.pk0112.a8. The sequence of this contig is shown in SEQ ID NO:19; the deduced amino acid sequence of this contig is shown in SEQ ID NO:20. A contig was assembled using the sequence from a portion of the cDNA insert in clones wkm1c.pk0002.g6 and wr1.pk0046.c10. The sequence of this contig is shown in SEQ ID NO:21; the deduced amino acid sequence of this contig is shown in SEQ ID NO:22.

The BLASTX search using the nucleotide sequences mentioned above revealed similarity of the proteins encoded by the cDNAs to sucrose phosphate synthase from different species. The BLASTX results for each of these sequences are shown in Table 4:

TABLE 4

BLAST Results for Clones Encoding Polypeptides Homologous to Sucrose Phosphate Synthase

| Clone | Organism | NCBI General Identifier No. | pLog Score |
|---|---|---|---|
| ncs.pk0009.e3 | Craterostigma plantagineum | 3915021 | 105 |
| bsh1.pk0013.d3 | Saccharum officinarum | 1854378 | 90 |
| ceb5.pk0081.g10 | Musa acuminata | 3237273 | 27.3 |
| Contig of p0130.cwtaf69r p0093.cssan39r p0094.cssst68r p0119.cmtoh35r p0127.cntag51r | Craterostigma plantagineum | 3915021 | >250 |
| Contig of rls12.pk0024.d8 r10n.pk0002.e3 | Saccharum officinarum | 1854378 | 131 |
| r10n.pk086.i23 | Saccharum officinarum | 1854378 | 58.7 |
| r10n.pk0056.d5 | Saccharum officinarum | 1854378 | 68.4 |
| sfl1.pk0048.a12 | Citrus unshiu | 3915023 | >250 |
| sfl1.pk0075.d7 | Craterostigma plantagineum | 3915022 | 56.7 |
| Contig of wr1.pk0112.a8 wr1.pk0028.h11 | Saccharum officinarum | 1854378 | >250 |
| Contig of wkm1c.pk0002.g6 wr1.pk0046.c10 | Zea mays | 401114 | 84.5 |

FIG. 1 presents an alignment of the amino acid sequences set forth in SEQ ID NO:2 and SEQ ID NO:16 with the *Citrus unshiu* sequence (SEQ ID NO:23). The *Citrus unshiu* sequence is 75.1% identical to the amino acid sequence presented in SEQ ID NO:2 and 83.3% identical to the amino acid sequence presented in SEQ ID NO:16.

The BLASTX search also revealed that of two sugarcane sucrose phosphate synthase amino acid sequences (NCBI General Identifier Nos. 1854376 and 1854378), one of these sequences (NCBI Gene Identifier No. 1854376) displayed considerably more homology to the corn sucrose phosphate synthase amino acid sequence disclosed in U.S. Pat. No. 5,665,892 (NCBI Gene Identifier No. 168626). Accordingly, the nucleic acid fragments described in Table 4 may therefore be classified as encoding polypeptides similar to the corn SPS disclosed in U.S. Pat. No. 5,665,892 or similar to the sugar cane SPS set forth in NCBI Gene Identifier No. 1854378. Using this criterion, the amino acid sequences set forth in SEQ ID NO:2, SEQ ID NO:18 and SEQ ID NO:22 are similar to the SPS sequence disclosed in U.S. Pat. No. 5,665,892, whereas amino acid sequences set forth in SEQ ID NO:4, SEQ ID NO:6, SEQ ID NO:8, SEQ ID NO:10, SEQ ID NO:12, SEQ ID NO:14, SEQ ID NO:16 and SEQ ID NO:20 encode a different SPS that is similar to the sugar cane SPS set forth in NCBI Gene Identifier No. 1854378.

FIG. 2 presents an alignment of the amino acid sequence set forth in SEQ ID NO:8 with the corresponding region of the corn sucrose phosphate synthase amino acid sequence (SEQ ID NO:24) disclosed in U.S. Pat. No. 5,665,892. The sequence disclosed in U.S. Pat. No. 5,665,892 is 67.7% similar to the amino acid sequence presented in SEQ ID NO:8, clearly indicating that the corn amino acid sequence presented in SEQ ID NO:8 is distinct from the sucrose phosphate synthase amino acid sequence disclosed in U.S. Pat. No. 5,665,892.

Sequence alignments and percent similarity calculations were performed using the Megalign program of the LASER-GENE bioinformatics computing suite (DNASTAR Inc., Madison, Wis.). Multiple alignment of the sequences and percent similarity calculations were performed using the Clustal method of alignment (Higgins, D. G. and Sharp, P. M. (1989) *CABIOS.* 5:151–153) using the default parameters (GAP PENALTY=10, GAP LENGTH PENALTY=10).

BLAST scores and probabilities indicate that the instant nucleic acid fragments encode entire soybean and substantial portions of barley, corn, Catalpa, rice, soybean and wheat sucrose phosphate synthase enzymes that are distinguishable from other sucrose phosphate sequences known in the art. These sequences also represent the first barley, Catalpa, rice, soybean and wheat sequences encoding the instant sucrose phosphate synthase protein.

Example 4
Expression of Chimeric Genes in Monocot Cells

A chimeric gene comprising a cDNA encoding a sucrose biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Boulevard, Manassas, Va. 20110-2209 USA), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL1-Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a sucrose biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5
Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J Biol. Chem.* 261:9228–9238) can be used for expression of the instant sucrose biosynthetic enzyme in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding a sucrose biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the sucrose biosynthetic enzyme and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6
Expression of Chimeric Genes in Microbial Cells

The cDNAs encoding the instant sucrose biosynthetic enzyme can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding sucrose biosynthetic enzyme are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having sucrose phosphate synthase activity, wherein the amino acid sequence of the polypeptide and the amino acid sequence of SEQ ID NO:16 have at least 95% identity based on the Clustal alignment method using the default parameters, or
   (b) the full complement of the nucleotide sequence.

2. The polynucleotide of claim 1, wherein the nucleotide sequence comprises the nucleotide sequence of SEQ ID NO:15.

3. The polynucleotide of claim 1, wherein the polypeptide comprises the amino acid sequence of SEQ ID NO:16.

4. A chimeric gene comprising the polynucleotide of claim 1 operably linked to a regulatory sequence.

5. A method for transforming a cell comprising transforming a cell with the polynucleotide of claim 1.

6. A cell comprising the chimeric gene of claim 4.

7. A method for producing a transgenic plant comprising transforming a plant cell with the polynucleotide of claim 1 and regenerating a plant from the transformed plant cell.

8. A transgenic plant comprising the chimeric gene of claim 4.

9. A seed comprising the chimeric gene of claim 4.

* * * * *